US008000979B2

(12) United States Patent
Blom

(10) Patent No.: US 8,000,979 B2
(45) Date of Patent: Aug. 16, 2011

(54) AUTOMATED PATIENT MANAGEMENT SYSTEM

(76) Inventor: Michael G. Blom, Odessa, FL (US)

( * ) Notice: Subject to any disclaimer, the term of this patent is extended or adjusted under 35 U.S.C. 154(b) by 1146 days.

(21) Appl. No.: 11/286,905

(22) Filed: Nov. 23, 2005

(65) Prior Publication Data

US 2006/0111941 A1    May 25, 2006

Related U.S. Application Data

(60) Provisional application No. 60/630,937, filed on Nov. 24, 2004.

(51) Int. Cl.
*G06Q 50/00* (2006.01)
*G06Q 10/00* (2006.01)
(52) U.S. Cl. .............................. 705/2; 705/3
(58) Field of Classification Search .................. 705/2
See application file for complete search history.

(56) References Cited

U.S. PATENT DOCUMENTS

| | | | |
|---|---|---|---|
| 4,491,725 A | | 1/1985 | Pritchard |
| 5,748,907 A | * | 5/1998 | Crane ............................... 705/2 |
| 5,760,704 A | | 6/1998 | Barton |
| 5,822,544 A | | 10/1998 | Chaco |
| 5,832,447 A | | 11/1998 | Rieker |
| 5,845,261 A | | 12/1998 | McAbian |
| 5,890,129 A | | 3/1999 | Spurgeon |
| 5,913,197 A | | 6/1999 | Kameda |
| 5,923,018 A | | 7/1999 | Kameda |
| 5,970,466 A | | 10/1999 | Detjen |
| 5,991,730 A | | 11/1999 | Lubin |
| 6,047,259 A | * | 4/2000 | Campbell et al. ................. 705/3 |
| 6,112,986 A | | 9/2000 | Berger |
| 6,321,203 B1 | | 11/2001 | Kameda |
| 6,345,260 B1 | | 2/2002 | Cummings |
| 6,421,649 B1 | * | 7/2002 | Rattner ............................. 705/2 |
| 6,488,205 B1 | | 12/2002 | Jacobson |
| 2001/0011680 A1 | | 8/2001 | Soltesz |
| 2001/0037226 A1 | * | 11/2001 | Kurokawa ......................... 705/5 |
| 2002/0072934 A1 | | 6/2002 | Ross |
| 2002/0107769 A1 | | 8/2002 | Dashefsky |
| 2002/0123908 A1 | | 9/2002 | Ando |

(Continued)

FOREIGN PATENT DOCUMENTS

EP    0696006 A2    2/1996

(Continued)

OTHER PUBLICATIONS

Armando, Benchmarking the perioperative process. I. Patient routing systems: A method for continual improvement of patient flow and resource utilization, Journal of Clinical Anesthesia, vol. 9, Issue 2, Mar. 1997, pp. 159-169.*

(Continued)

*Primary Examiner* — Luke Gilligan
*Assistant Examiner* — Tran (Ken) Nguyen
(74) *Attorney, Agent, or Firm* — Lewis Brisbois Bisgaard & Smith LLP

(57) ABSTRACT

A system for making the process of registering at and receiving treatment in a healthcare facility more efficient and safe has been developed. The system utilizes computer communications network-based systems, software, various input and output stations, and a patient identification card (e.g., Loyalty Card) that work together to allow (a) providers to direct, track, and optimize the efficiency of patient activity and (b) patients to have ready access to their status and, in some cases, control of the healthcare process.

1 Claim, 36 Drawing Sheets

U.S. PATENT DOCUMENTS

| | | |
|---|---|---|
| 2002/0156672 A1 | 10/2002 | Burko |
| 2003/0088441 A1 | 5/2003 | McNerney |
| 2004/0019501 A1 | 1/2004 | White |
| 2004/0186744 A1 | 9/2004 | Lux |
| 2004/0249250 A1 | 12/2004 | McGee |
| 2004/0267575 A1* | 12/2004 | Boing .............................. 705/3 |
| 2005/0043964 A1 | 2/2005 | Thielscher |
| 2005/0049910 A1 | 3/2005 | Lancaster |
| 2005/0055246 A1 | 3/2005 | Simon |
| 2005/0187948 A1 | 8/2005 | Monitzer |
| 2005/0209886 A1 | 9/2005 | Corkern |

FOREIGN PATENT DOCUMENTS

| | | |
|---|---|---|
| EP | 1160716 A2 | 12/2001 |
| JP | 09167176 A | 6/1997 |
| WO | WO 9115817 A1 | 10/1991 |
| WO | WO 9922330 A1 | 5/1999 |
| WO | WO 0201483 A2 | 1/2002 |

OTHER PUBLICATIONS

Porter, Stephen C. et al.: "The asthma kiosk: A patient-centered technology . . . ;" J of the American Med Info Assoc, vol. 11, 2004, pp. 458-467, Abstract only.

Takada, Masahiro et al.: "Benefits and risks of electronic patient . . . ;" Jap Journal of Nat Med Services, vol. 59, 2005, pp. 255-261, Abstract only.

Goldschmidt, L. and G.L. Goodrich: "Development and evaluation of a point-of-care interactive . . . ;" J of Telemedicine and Telecare, vol. 10, 2004, p. S1-30-2, Abstract only.

Galvanon: Product Description "MediKiosk", 2002-2006.

* cited by examiner

CARD SYSTEM DATABASE TABLES

Entity Relationship Diagram (ERD)

PATIENT ◼ EASE

PATIENT ■ EASE

PATIENT @ EASE

Patient Arrival Board

| GEORGE,J | Loyalty Cardholder |
|---|---|
| MARGE,J | |

FIG. 22

AUTOMATED PATIENT MANAGEMENT SYSTEM

CROSS-REFERENCE TO RELATED APPLICATION

The present application claims the priority of U.S. provisional patent application No. 60/630,937 filed Nov. 24, 2004.

FIELD OF THE INVENTION

The invention relates generally to the fields of healthcare and information technology. More particularly, the invention relates to a system for managing patients in a healthcare facility.

BACKGROUND

Existing systems for automating healthcare have focused on addressing the needs/desires of providers, not patients. As a result, patients often have to endure long waiting times and poor customer service. To alleviate this problem, a system is needed that both maximizes the efficiency of the healthcare process and provides patients easy access to their status and/or control of the process.

SUMMARY

The invention relates to the development of an automated healthcare system that addresses the needs and desires of both healthcare providers (e.g., patient service workers and clinicians) and patients. The system encompasses computer communications network-based systems, software, various input and output stations, and a patient identification device (e.g., an identification card, an RFID, or a smartcard) that work together to allow (a) providers to direct, track, and optimize the efficiency of patient activity, and (b) patients to have ready access to their status and, in some cases, control of the healthcare process.

The system improves patient satisfaction by reducing wait times to be seen by a clinician and improving communication to the patient, patient service workers, and hospital management. By employing provider-accessible and patient-accessible information input/output stations such as a touch-screen kiosk, the system provides direct patient access to complete and accurate patient-specific information. The system also effectively establishes a process of managing waiting lines in any given area and then automatically and electronically linking to the next area. For example, for a patient visiting a healthcare facility for a physical examination and diagnostic radiology, after the patient has completed the check-in process (e.g., registration), the system can automatically place the patient in the queue for the physical examination or the diagnostic radiology. To enhance the efficiency of this process, the system preferably prioritizes which service is delivered first according to expected wait times. For example, if the expected waiting time for physical examination is longer than that for radiology, the patient would first be put on the radiology queue. On the other hand, if the expected waiting time for radiology is longer than that for physical examination, the patient would first be put on the physical examination queue.

In one embodiment of the invention, an enterprise information system provides a real-time picture of the flow of patients throughout the organization. Patient service workers and clinicians can view the details of what is occurring in registration and treatment departments, thereby enabling them to make changes to improve the efficiency of patient flow (and thereby improving revenue generation). Patients are informed of their process stage and queue status through an information output device such as a large video display. The display may optionally be outfitted to display audiovisual entertainment, general medical information, points of interest, and advertisements.

Accordingly, the invention features a system for managing a plurality of patients in a healthcare facility. The system includes at least one server communicatively connected to a computer communications network, the at least one server including at least one database having stored therein data relating to the plurality of patients, the data including (a) names of the plurality of patients, (b) names of at least two departments within the healthcare facility, (c) at least one listing of names of at least two patients of the plurality of patients who are queuing to visit one of the at least two departments, (d) demographic information pertaining to the plurality of patients, and (e) treatment status of each patient of the plurality of patients, the at least one server configured to receive input signals from and transmit output signals across the computer communications network to a network access device that is accessible by the plurality of patients and to a network access device accessible to staff of the healthcare facility, at least one patient identification card for facilitating checking-in to the healthcare facility by at least one patient of the plurality of patients, a means for determining an order in which the plurality of patients will visit the at least two departments, and at least one screen displaying the order in which the plurality of patients will visit the at least two departments that is publicly displayed within the healthcare facility. The network access device that is accessible by the plurality of patients can be, for example, a kiosk, video display, PDA, computer monitor, or television monitor. The network access device that is accessible to the staff of the healthcare facility can be, for example, a computer monitor or a television monitor. The at least one screen can further display advertisements, news and weather reports. At least a portion of the data stored in the database can be modified by at least one of the plurality of patients via the input signals conveyed across the computer communications network. The means for determining the order in which the plurality of patients will visit the at least two departments includes a computer program executing business rules.

In another aspect, the invention features a method of managing a plurality of patients in a healthcare facility. The method includes the steps of: (a) providing at least one server communicatively connected to a computer communications network, the at least one server including at least one database having stored therein data relating to the plurality of patients, the data including (i) names of the plurality of patients, (ii) names of at least two departments within the healthcare facility, (iii) at least one listing of names of at least two patients of the plurality of patients who are queuing to visit one of the at least two departments, (iv) demographic information pertaining to the plurality of patients, and (v) treatment status of each patient of the plurality of patients, the at least one server configured to receive input signals from and transmit output signals across the computer communications network to a network access device that is accessible by the plurality of patients and to a network access device accessible to staff of the healthcare facility; (b) providing a means for determining an approximate amount of time each patient of the plurality of patients will wait before receiving treatment; (c) accepting at the server an input signal transmitted across the communications network from the network access device accessible to staff of the healthcare facility, the input signal including data such as (i) the name of at least one patient of the plurality of patients, (ii) the name of at least one department within the healthcare facility, and (iii) demographic information pertaining to the at least one patient, and storing the data included in the input signal in the database; and (d) transmitting from the server an output signal including at least a portion of the data included in the input signal and an approximate amount of time the at least one patient will wait before receiving treatment across the communications network to the network access device accessible by the plurality of patients.

As used herein, the phrase "computer communications network" means a group of two or more computer systems communicatively linked together. For example, a "local area network" or "LAN" is a computer communications network where the linked computers are geographically close together (e.g., in the same building). A "wide area network" or "WAN" is another computer communications network similar to a LAN except that the linked computers are farther apart (e.g., they are in different buildings and connected by telephone lines or radio waves). A "global" computer communications network is one that is not limited to a certain geographical area or number of individual computers, but rather links computers throughout the world generally without restriction. The Internet is an example of a global computer communications network.

As used herein, the term "server" means a computer or device on a network that manages network resources, e.g., processes data coming in from a computer communications network, stores files in a database, and outputs files from a database over the computer communications network. Examples of servers include file servers, e-mail servers, and Web servers.

"Computer program" and "program" mean a writing that sets forth instructions that can direct the operation of an automatic system capable of storing, processing, retrieving, or transferring information. When a computer program is entered into a computer system, it forms part of the system referred to as "software." By the term "hardware" is meant physical components of a computer system.

As used herein, a "Web site" is a site (location) on a computer communications network such as the Internet containing one or more Web pages. Most Web sites contain a "home page," which is the main page of a Web site and usually the first screen users see when they enter the site. Home pages often offer an introduction to the material contained in the Web site and also an index or table of contents hyperlinked to related Web page documents of the site.

By the term "user" is meant any individual or entity who accesses or uses the system of the invention.

Unless otherwise defined, all technical and legal terms used herein have the same meaning as commonly understood by one of ordinary skill in the art to which this invention belongs. Although methods and materials similar or equivalent to those described herein can be used in the practice or testing of the present invention, suitable methods and materials are described below. All patent applications mentioned herein are incorporated by reference in their entirety. In case of conflict, the present specification, including definitions, will control. In addition, the particular embodiments discussed below are illustrative only and not intended to be limiting. Other features and advantages of the invention will be apparent from the following detailed description, and from the claims.

BRIEF DESCRIPTION OF THE DRAWINGS

FIGS. 7-36 are screen shots of an aspect of the present invention.

DETAILED DESCRIPTION

Figure 1:
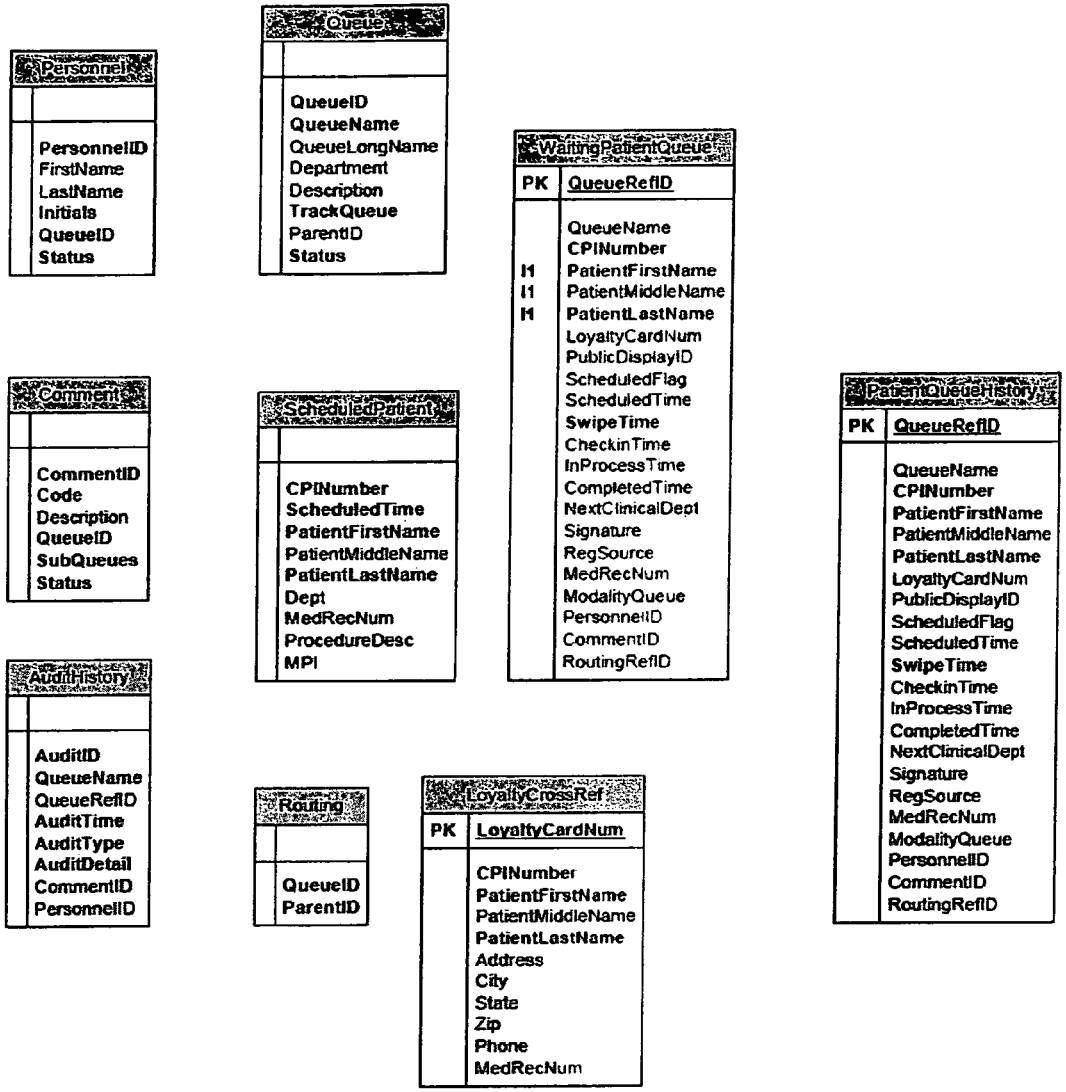
FIGS. 1 and 2 are entity relationship diagrams.

The below described embodiments illustrate various representative systems within the invention. Nonetheless, from the description of these embodiments, other aspects of the invention can be made and/or practiced based on the description provided below.

An exemplary automated patient management system features a computer communications network-based system, software, various information input and output stations or devices (e.g., network access devices), and a patient identification device (e.g., identification card, RFID, smartcard). Software useful in the invention is configurable to allow customization to meet the needs of each healthcare facility, provides management of queues, sub-queues, and modalities with and without application of user-defined business rules to facilitate patient recognition, check-in and provide feedback, queue information, weather, news, and marketing information to the patient as well as customer service-like features to the patient to enhance the quality of their visit to the healthcare facility. The system provides real-time and, by virtue of its database, historical information to supervisory and managerial levels both to address real-time bottlenecks at all connected modalities and to identify the quality of the work effort of hospital employees. The input stations include two categories, those which enable the patient to directly interact with the system to initiate services related to their visit and to request information related to their visit, and those which enable hospital employees to better manage the patient queues to accelerate their entry into the healthcare facility. The input stations can be any Web-enabled or PC-connected device including personal computers, tablets, laptops, kiosks, card-readers (bar code, magnetic stripe, and smart card), biometric readers, RFID readers, etc. The output stations provide the patient with patient-specific information and status (e.g., patient scheduled visits, face sheets, etc.), patient queue information, patient instructions, weather, news, and marketing information (e.g., advertisements), healthcare facility news, and any desired content. Output stations also provide for health information and identification (e.g., Loyalty Card) production both at the facility and remotely at sites external to the healthcare facility (e.g., assisted living facilities, events, health fairs, etc.). These output stations include Web-enabled devices for delivery direct to the patient's computer as well as patient informational monitors, and identification card (e.g., Loyalty Card) printers. The input stations and output stations can be integrated into one device or they can be stand-alone devices. The patient identification device can be any suitable device such as an identification card, an RFID, and/or a smartcard, bio-metric device, and can adjust to utilize any magnetic stripe and/or bar-coded device. The identification device can also be placed on the patient's vehicle. The system is preferably configured to run on computer systems already in place at the healthcare facility, e.g., in a Windows/PC or UNIX-based environment.

The operation of the system can be illustrated through a typical patient visit to a healthcare facility such as a hospital or clinic. The system begins capturing data on patient flow as soon as the patient arrives at the healthcare facility and oversees patient movement from registration through treatment to departure. The system has the ability to perform its initial capture direct from a patient's computer prior to the patient's arrival at the healthcare facility.

In a preferred embodiment of the invention, the system features public screens that are displayed in different locations throughout the healthcare facility. By displaying patient queuing information, for example, the public screens can effect a dramatic reduction in patient questioning of the healthcare facility staff regarding how long they must wait before receiving treatment. These public screens can also display information that helps patients prepare for registration. The screens can be used as a marketing tool when set up to alternate between patient information screens and marketing messages (e.g., advertisements). Other examples of displays that can be viewed on the public screens are news and weather reports.

Additional functionalities of the system of the invention are numerous. For example, ADT linkage automatically updates system files. When face sheets are provided, erroneous information is identified before they go to the registrars. A benefactor lounge can be incorporated that allows key contributors to sign-in and be routed from any location while they receive the attention the healthcare provider chooses to provide. A valet service which moves patients in and out of the healthcare facility more quickly and easily is also envisioned. Marketing system connectivity allows a patient service worker to download potential patient files and tie-in to marketing programs and strategies. Identification card (e.g., Loyalty Card) functions include use as a health information card. When used at the healthcare facility gift shop or cafeteria, the identification card may entitle the patient to discounts. Such use improves business, track attendance at meetings, and remote registration.

EXAMPLE 1

Functional Hierarchy

One embodiment of the system of the invention combines a patient services application and a marketing services application. In one variation of this embodiment, eight major functions are defined within the patient services application. These eight major functions are: 1) check-in patient, 2) select patient (automatic or manual, business rules, scheduled vs. unscheduled, card privileges), 3) expedite patient registration, 4) complete and route patient (automatic routing, manual routing, alert next department), 5) enhance communication to patient, 6) communicate status to hospital administration and staff, 7) communicate patient information to external entities, and 8) maintain system.

In this system, a patient is provided a number of options to facilitate check-in to the facility by the use of an identification device (e.g., a bar-coded loyalty or identification card). The identification device can be delivered to the patient at check-in or preferably has already been placed in the possession of the patient, e.g., on a prior visit, at an event or from a marketing-related mailing. If the patient is not in possession of a bar-coded identification card (e.g., Loyalty Card), the receptionist checks the patient into the system by entering the patient's name. Check-in can be facilitated with the identification device or any other suitable identifying method, e.g., biometric (e.g., fingerprinting) or electronic methods. Regardless of the method used to check-in, the patient's name can be displayed on a Patient Tracking Display in the waiting area in addition to the receptionist and registrar workstations.

In some embodiments of the system, the patient has the ability to check-in to the facility before arrival by using a remote check-in function allowing the patient to enter an identifier such as a Loyalty Card number via a Website or a voice/touchtone-enabled telephone check-in. Check-in can also be accomplished when a patient is being transported in either a planned transport or an emergency transport situation.

In some embodiments of the invention, input devices such as personal digital assistants (PDAs) with wireless connection to the network and the check-in application software can be provided to parking valet personnel to check-in the patient as they leave their vehicles to be parked. The valet can enter the patient's identifier into the PDA to check the patient into the system.

Kiosks located at select sites within a healthcare facility and a community can be used for self check-in to the facility. For example, the patient can enter his identifier (e.g., swipe a Loyalty Card) and electronically sign on a signature pad or touch screen (such as one on a tablet PC or like device) to notify the system of his arrival, so that the system can automatically place the patient in the queue for the appropriate services. In some embodiments, the patient's name is displayed on a Patient Tracking Display (e.g., a video output) in the waiting area in addition to the receptionist and registrar workstations. An animated display in one corner of the kiosk's display guides and shows the patient the proper way to enter his identifier. Other features of the check-in portion of the system might include: a) import capabilities from the scheduling system enable the system to recognize the patient has a scheduled appointment; b) the ability to check-in to hospital events and marketing events, e.g., physician mixers and classes (such a system can hold data on which non-clinical events persons have attended by establishing an appropriate queue to capture attendees, counting and identifying who shows for an event); c) the ability to check-in to a physician's office or clinic; d) the ability to check-in a patient when arriving at the treatment department; e) identification card number look-up function for patients with cards but who forgot to bring them; f) patient pictures display at check-in with Loyalty Cards for patients that have had a previous treatment; g) the ability to register a patient in the patient's own language; h) captured signature can populate all necessary registration forms; i) wireless check-in by the registrar; and j) voice and handwriting recognition.

In preferred embodiments of the system, the patient services application is linked to the facility's security system to enable the patient access to a particular department or area within the facility. For example, a patient's identification device might be used as a key to unlock pre-selected doors. In this embodiment, only patients authorized by the system have the ability to unlock the pre-selected doors.

Once the patient has been checked-in (registered), a registrar or technician can select the next patient for registration in a registration area or for treatment at an ancillary department. This selection can be either by an automatic or manual method. The system provides for automatic system selection of "Next Patient" by virtue of its internal business rules engine (e.g., a scheduled patient may find himself with an increased priority as he approaches his scheduled time) and the system provides for manual selection for hospital employees to select from any patient residing in their assigned patient queue. Business rules can be applied to prioritizing which patients are selected that allow department management or administration to customize processing of information based on specific business rules or policies, e.g., patient placement on the check-in queue, notifications, VIP and special handling, scheduled vs. unscheduled, card privileges, management and administration notifications, status queue changes and wait time issues, user-configurable, and patient alert if a patient has not completed visits to all ancillary departments.

In a representative embodiment of the system, a patient's name can change color (e.g., normal ->yellow ->red) on a Master Administrative Screen of the system based on the elapsed time that a patient has remained in the queue in Checked-In Status based on user-definable time increments. The status of the patient record can be displayed as follows: YELLOW—after a set period of time has elapsed from check-in; RED—after an elapsed period of time from the change to YELLOW; and change to RED status can generate an e-mail notification to the appropriate department management. The presence of the patient's identifier (e.g., account number) on the identification device provides the registrar faster access to the patient's current demographic and insurance information from the information system that is used to register the patient. Although color is used in this example to indicate patient status, any suitable indicator can be used (e.g., text, symbols, shapes, etc.).

The identification device's patient identifier (e.g., a card having an identifying bar code) can be linked to the patient's medical record number to expedite the registration process by providing the patient the ability to update his demographic information without the involvement of the registrar. This can be accomplished by providing a capability for the patient to enter his information from either his own computer or a hospital resident computer where the registrar would only need to perform a validation function. The system also provides for automated update by virtue of its many import capabilities including File-Transfer and HL7 connection to any existing Hospital Information System (HIS) and by connection to any external data source which the hospital has requested to be loaded. If the patient decides not to self-register, the registrar can have access to updated demographic data provided by the patient on the facesheet (e.g., the general information related to each patient including demographic, address, and personal information printed by the kiosk).

To verify and retrieve a patient record, in one embodiment of the system, a patient swipes his identification card (a Loyalty Card, a driver's license, an insurance card or a credit card) into an input device to activate the system to access the patient's demographic information stored from a previous visit. The system can store static information such as demographic and clinical information, e.g., nutrition, special needs, blood type, advanced directives, organ donor, consent, insurance, allergies (e.g., food and drug), Medicare Advance Beneficiary Notice, Medicare Secondary Payer, PCP's UPIN, and a record of who/when accessed this information. In some embodiments of the system, a patient can request and review his registration information via a paper format printed by the kiosk. This assists in reducing the time with the registrar by reviewing and updating the information while waiting to see the registrar. Such a process can include the following steps. Upon swiping their card at the kiosk, the patient selects the option to review their information prior to Registration. The system requests the "face sheet" data from currently existing systems at the facility which contain this information, and then prints the information out for the patient. The patient reviews and corrects the information on the sheet, signs the sheet in the appropriate space, and brings that sheet with him when he goes to see the registrar. The registrar then updates only those fields that have changed.

Once the patient has verified his personal/demographic information without the aid of a registrar, the patient has the ability to register. The patient interacts with a kiosk screen instead of a registrar to accomplish the following functions: a) swipe card, capture signature and print forms; b) point of service registration by routing all pre-registered patients to point of service; c) automatic transfer from registration queue to treatment department; d) ability to know patient account status; e) use of fingerprint in addition to/in lieu of bar code; and f) use Hospital or multi-facility card to check-in.

The system can also provide the ability for server-to-server connectivity to allow a single Loyalty Card to work within a health network. The identification on a card identifies the health organization as well as the individual facility. If a patient from one facility comes to another facility, the server detects that they shared the same health network and can send a request to the appropriate server which does an ADT retrieval and send the information in a HIPAA-compliant method to the requesting server where a facesheet can be printed out to facilitate registration using this information.

Upon completion of registration, the registrar or the system can indicate that delivery of a particular service to a patient is complete and then can route the patient to the next department. An alert can be sent to the next department that the patient will soon arrive. An alert can also be sent to the preceding department that it is ready for the next patient.

As described above, a Patient Tracking Display can be used to show the names of the patients in the waiting area, providing estimated wait times showing current wait times in addition to the capability to display green/yellow/red indicators that have been determined and configured within the system. This display can have multi-language display capabilities. Some embodiments of the system allow inquiry into wait times. For example, a patient identifier can be used as a key to access components of the system remotely via the internet or a telephone-voice response system to acquire information and a status update. A website can be used for a real-time inquiry to the current wait times, and can contain logic to look at the historical basis and recommend times when the wait time is lowest. The system might provide these additional functions: auto alert throughout the facility so that a patient does not need to wait in the waiting area for his turn to be called, Internet café hooked up to system (to keep patients occupied during waiting time), and auto-notification of delays in appointments to a patient's network access device of choice.

The input/out devices (e.g., kiosks) of the system can provide a variety of information services to the patient, e.g., a) print maps and directions to different departments within the hospital and to hospital-associated facilities and physicians outside of the hospital, b) itinerary/where to go, c) kiosks having a touch screen with major areas as buttons and when pressed, an Itinerary and a map is displayed on the screen and available for printout, c) physician directory, d) Internet access, e) print patient demographics verification form, f) patient financial responsibility and account status, g) facility directory, discount coupons by card type, and wait time, h) products/services look up, i) in-house department and physician contact information with pictures of physicians and key individuals, j) department and clinic hours, k) outside physicians' directory, l) marketing content displayed on Patient Tracking Display or the ability to run an advertising window on a Patient Tracking Display in conjunction with the patient status, m) on-line application for Loyalty Cards, n) copies of test results over the Web (e.g., using Loyalty Card number), o) access to/from physician and service provider offices (a functionality that allows linkage between Loyalty Card and patient information maintained in a hospital's systems for physician office look up of patient face sheet information through the use of the Loyalty Card Number), and p) the Patient Advantage Room Function. The Patient Advantage Room Function includes: a) a separate room, b) use of a swipe card to open the door to the room, c) gold and platinum feature providing free beverages, and d) snacks and screens in the room showing the queues around the hospital. In this embodiment, a service person sits in the room, swipes the patient's card, and puts the patient into the appropriate queue, and has access to an inquiry dashboard so that they can give the patient the current average wait time. This room would be for those, for example, who have multiple tests that day, or a place to go to after a test.

Various embodiments of the system can also feature a patient locator function that provides the ability to locate a patient who has checked-in through a registration area for treatment. This tracks the "path" of the patient through the care event and locates the last point of contact (information desk "patient finder").

As described above, the system can be set up to communicate a patient's status to a healthcare facility's administration or staff. For example, the system can be set up so that administration is notified of the arrival of a Board member or other VIP at check-in by e-mail and/or pager messages. In some embodiments of the system, the appropriate department management is notified of excessive patient waiting times by e-mail and/or pager messages.

In one embodiment, once the patient has completed the healthcare facility visit and is ready to leave the facility, an e-mail message is sent to the PDA of the healthcare facility's valet. This enables the valet to have the patient's vehicle ready at the entrance to the facility. Valets are preferably provided with equipment which can recognize Loyalty Cards. In this embodiment, a patient arrives, their card is recognized, a valet welcomes the patient by name, provides the patient with a current parking card and parks the patient's car. When the patient is ready to retrieve his car (potentially at the treatment location), he swipes his card and chooses to get the car ready. The valet is then notified to get the car and parks the car in one of the loyalty parking spots. When the patient arrives, he has his card scanned to confirm ownership, receives his keys, walks to his car, and departs without having to wait.

To facilitate archival, reporting and analysis functions (e.g., provide tracking and performance data), in one embodiment of the system, the database maintains data for swipe-in times at registration and ancillary departments. This process typically includes MIS Reports, sign-in logs archive of the signatures, export to spreadsheet, real-time statistics, and Patient Flow Simulator (to take historical production information and use it for simulations changing individual components of the day's activities). Based upon MIS reporting, an area of possible congestion/slow-down is identified. The simulator provides some possible causes for the slow-down staffing. An authorized hospital employee selects one of the "system-identified" resources to change. The system calculates and demonstrates how the change in that resource affects patient time. The system includes automatic notification to the I.T. (information technology) or technical support staff (by e-mail) of processing or database errors if and when they occur as well as an audit trail. The audit trail provides the ability to track specific types of transactions within the patient services application for audit and issue resolution purposes. This audit functionality can be implemented as a history table which can store the following: department identifier, date/time, transaction type, transaction detail, audit reason code, and user identifier (person performing the action). When the auditable transaction is performed, the required information is copied to a record in the audit history table, and prior to completing the transaction, the user is presented with a user identifier window to identify who was making the transaction, and a reason code.

The system includes methods of communicating patient information to external entities. For example, e-mail notifications can be sent to external entities and business partners indicating that a patient has been registered at the facility.

In some embodiments of the system, the patient can request taxi service. To summon a taxi to the facility to take them home, the patient swipes their card and the swipe generates an e-mail message which is sent to a participating taxi service that notifies the dispatcher to send a taxi to the facility for the patient. Upon completion of treatment, the patient swipes their Loyalty Card and selects taxi request. The system sends an e-mail and/or fax to the designated taxi service providing the patient's name and the location at which to pick up the patient. The patient accomplishes the request without having to go to a phone, asking someone to make the call, or having to pay for the call.

To notify a physician's office that the patient has been registered at the healthcare facility, the patient's primary care physician or other physician can be alerted by e-mail that the patient has been registered at the facility for treatment or tests. In some embodiments of the system, suppliers can be alerted by e-mail that the patient may require certain services such as oxygen. The patient's pharmacy can be notified that prescriptions have been requested by the healthcare facility.

As described above, the system provides a pre-installation function that can identify a communication/network method (wire/wireless), set-up parameter values, and establish patient flows. The capability is provided to establish and maintain the following system tables: queues, personnel, comments, routing, business rules, and audit capability.

In a system of the invention, eight major functions are defined within the marketing services application. These functions include: set-up batch system, receive and place batch files, automatically process batch files, export data (outside bulk priming, marketing database upload), register patient, produce remote Loyalty Cards, modify master records (update patient information in card database, activate/deactivate card), and support marketing initiative. Within set-up batch system are the following three functions: configure card, configure and start card service, and configure and start polling service.

In some embodiments of the system, a configure card function provides the capability to select the fields that will print on a card, in effect creating a card template. In this system, the function of the card service module is to receive records from the polling service, validate the record, update the marketing services database if certain criteria match, and print the cards where indicated as determined by INI file settings. The card service configuration values are defined and stored in the card services INI file. The function of the polling service in this system is to poll the directories and when valid records are found in these specific directories, the polling service sends the record to the card service. The polling service configuration values are defined and stored in the polling services INI file.

In some embodiments of the system, the receive and place batch files function imports batch records into the marketing services master database by placing them into a directory that has been identified on the server running the application. These batch files are in a specific format and can be from various sources such as an external marketing or CRM system. Additional sources may include associates lists, employee lists, physician's list, and others.

The automatically process batch files function continuously polls the input directories checking to see if any files have been copied or moved into these directories. As soon as the batch files are placed in the specified directories, the marketing service application reads each record in the files and begins the processing depending on the configuration of the polling service INI file. This automated process performs a match for every record read from the batch, and for every match then based on the configuration established will: Insert Only (insert when no match, no action on match), Insert/Update (insert when no match, update when match), and No Action. For each record processed, a print option is performed depending on the configuration: Print on Insert, Print on Update, Print on Match, or No Print. Optionally, the data is saved.

In this system, the marketing services application has the ability to export all or part of the database for outside bulk printing of Loyalty Cards in addition to being able to support an upload to an external Marketing Database. Two major functions are defined within Register Patient. The Receive and Store HIS Data function receives ADT (admission, discharge and transfer) information from the hospital information system and stores relevant demographic information to be used by the marketing services application. The Produce Loyalty Card function entails searching the database and allows the selection of which card is to be printed in addition to a selection screen which allows the selection of which fields are to be printed on the card to create a basic or full card. The cards preferably do not contain any patient-identifiable information, so there are no privacy concerns if the card is lost.

In one embodiment of the system, four major functions are defined within Produce Remote Loyalty Cards: set-up remote PCs, register customers and patients, print cards, and update master system from remote. The Set-up Remote PC's function provides the capability to export records from the marketing services master database into a laptop's remote database so that the two databases are synchronized at the time the laptop is scheduled to be at the remote event. The Register Customers and Patients function gathers patient/loyalty data at community events for remote data entry and pre-registration in the field. This information is loaded into the marketing services master database so that when the patient arrives at the hospital, he is recognized by the patient services application. In this embodiment, physician office data entry allows for pre-registration and loyalty tracking, as well as the gathering of pre-registration information at the initial point of contact. This function can also be extended to attendance event counting, providing the ability to take a laptop, load the current marketing services master database and go to a hospital event, read attendees' cards as they arrive, as well as keep track of counts. Additionally, information can be provided to marketing such as the number of events, a person's name, personal info, etc.

The Print Card function provides for a card being produced for the patient once the registration function has been completed. In addition, the capability is provided to search the remote database and allow the selection of which card is to be printed in addition to a selection screen which allows the selection of which fields are to be printed on the card to create a basic or full card. The cards preferably do not contain any patient-identifiable information, so there are no privacy concerns if the card is lost.

The Update Master System from Remote function provides the capability to export the records from a laptop's remote database into the marketing services master database so that the master database contains the updated records from the remote event.

In one embodiment of the system, the Modify Master Records function provides the ability to update patient information in the marketing services master database. Existing records can be updated or flagged as deleted as well as the ability to activate/deactivate so information can be corrected and the integrity of the database maintained. This database maintenance functionality can also be extended to a remote Customer Service organization as well as providing a Web-based Loyalty Card Request form that can be used by a prospective patient to request a Loyalty Card by submitting the necessary information required to provide the card.

Systems described herein can include a support marketing initiative. Two major functions are defined within a support marketing Initiative. The Develop Custom Reports function is a Report Writer function that enables custom reports to be defined and run against the marketing services master database. This Report Writer relies on flexibility to create ad hoc reports as well as to potentially acquire predefined standard reports. The Print Coupons function provides the capability to produce discount coupons that can be used or redeemed at the facility.

In various embodiments of the invention, the system supplements and supports marketing systems and is a tool in support of marketing departments. This is because current hospital systems have medical records systems where everyone must have a medical record number, almost always meaning they have visited the hospital at least once. The system of the invention, however, can hold information on potential visitors as well as those who have visited. While hospitals will export data from their main HIS and send the data to marketing companies, the system of the invention provides for the importing of files and holding of the information. This may provide registration improvement by allowing data from the system to automatically import to the main HIS.

Figure 2:
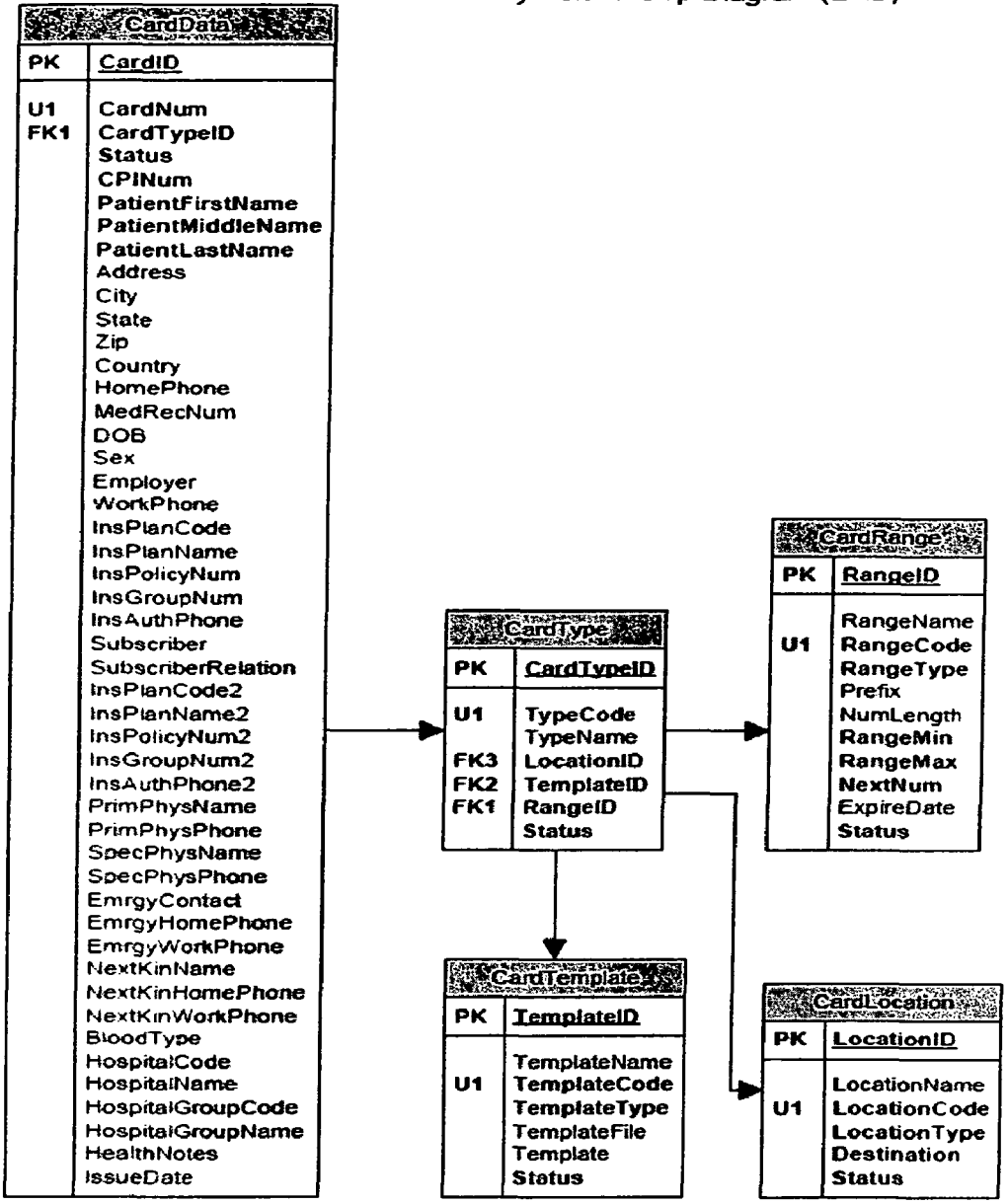

An Entity Relationship Diagram is shown in FIG. 1. This diagram depicts the database construct for the patient services application. The Entity Relationship Diagram shown in FIG. 2 depicts the database construct for the marketing services application. As described above, one embodiment of the system of the invention combines a patient services application and a marketing services application. In this system, the patient services application electronically checks-in a patient for registration, and then, upon completion of the registration process, notifies the receiving treatment department and tracks patient progress as the patient moves through the patient care event. The marketing services application captures and holds data for each identification card (e.g., Loyalty Card) holder. The marketing services application allows for the individual and batch membership information entry for cardholders, and the printing of cards, either individually or in a batch mode. The data that is contained in each identification card's record can be added and/or updated three different ways: the data can be imported using a batch process, imported by an HL7 ADT interface, and by a Remote Event Membership Entry function.

In some embodiments of the system, the patient services application has four primary system components: a) a check-in device that allows the patient to either check-in automatically using a Patient Identification Card, or manually if the patient does not have a card (e.g., this is a first time visit), b) a Patient Tracking Arrival Display identifying patients in an appropriately secure fashion, c) workstation-based administrative functions that allow the registrar to select patients for registration, and notify the treatment department once registration processing has been completed, and d) the system electronically captures and stores the patient's signature along with the date and time information, eliminating the requirement for a paper patient sign-in sheet.

Upon completion of the registration process, the application notifies the "receiving" ancillary treatment department that the registration process is complete and that the patient is "in-transit" to that department, effectively setting them up automatically for check-in. At the ancillary treatment department, the process resumes with the patient presenting himself to the department receptionist and checking in to that department and modality (if applicable). The receptionist and treatment department personnel then process their patient queue similar to registration queue processing. When treatment is complete, the ancillary treatment department can either close out the patient record or continue by notifying the next treatment department that the patient is in transit, and the process repeats.

In some embodiments of the system, the marketing services application has four primary system components. A first component is a Card Print Request. This function can be used mainly by the various registration areas and by other areas of the facility that need to generate individual cards. This function allows for the on-demand printing of individual card information already contained within the identification card (e.g., Loyalty Card) database. A second component is a Remote Event Membership Entry and Print. This function can be used by various departments to take the identification card (e.g., Loyalty Card) system to off-site functions and events so identification card membership can be promoted and entered into the system. When an identification card membership is entered into the database, a card is generated for the individual who provided the membership information. Once this information is collected, the remote system is brought back to the facilities Data Center where the data can be added into the Master identification card database. A third component is an Import and Export of the Database. This function allows identification card records to be passed between the Master database residing on the server and the Remote database residing on the Laptop computer(s) to be used for identification card membership collection at off-site functions and events. A fourth component is a Membership Batch Processing. This function is the processing of identification card membership information in a batch format. These batches can be from an external Marketing System or from other internal systems such as payroll or volunteer lists.

In the system, the marketing services application relies on these aforementioned back-office processes such as the HL7 data feed, the Membership Batch Processing function, and the Master & Remote Database synchronization to enter the data into the identification card database for printing and searching purposes. The marketing services application can also be utilized by the patient services application to obtain data related to the unique identification card number that is generated and maintained by the marketing services application.

EXAMPLE 2

System Overview

Figure 3:
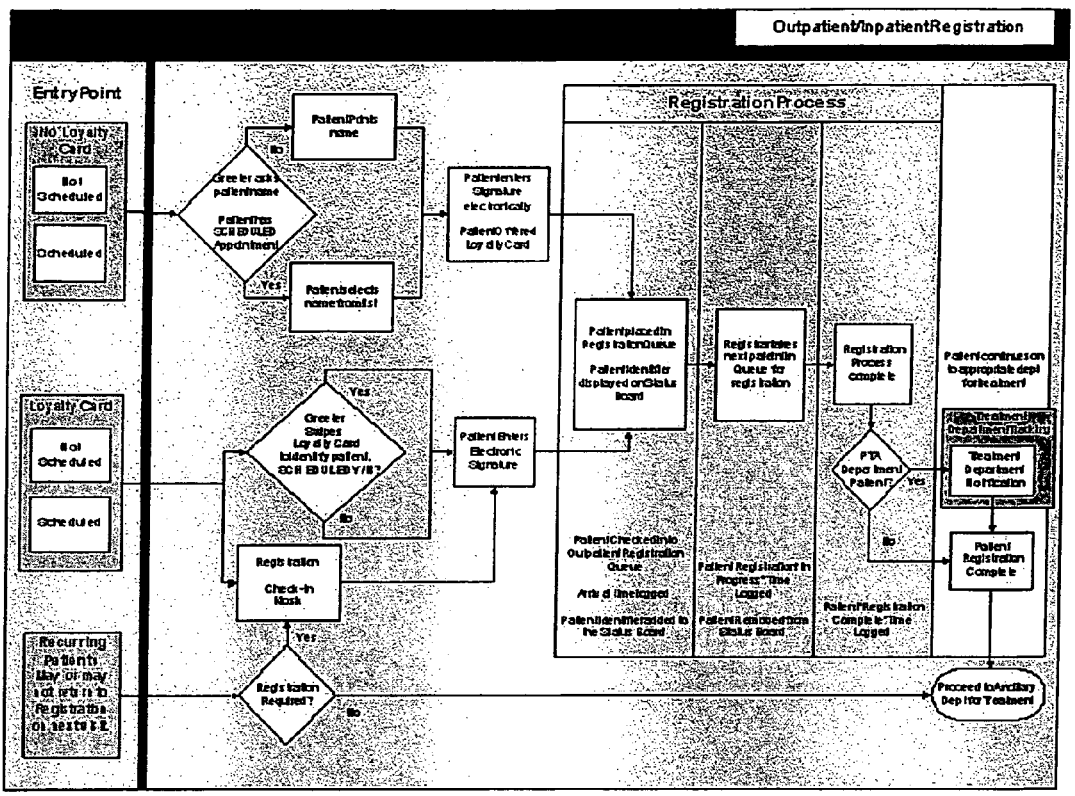
FIGS. 3 and 4 are flowcharts of an aspect of the present invention.
Figure 4:
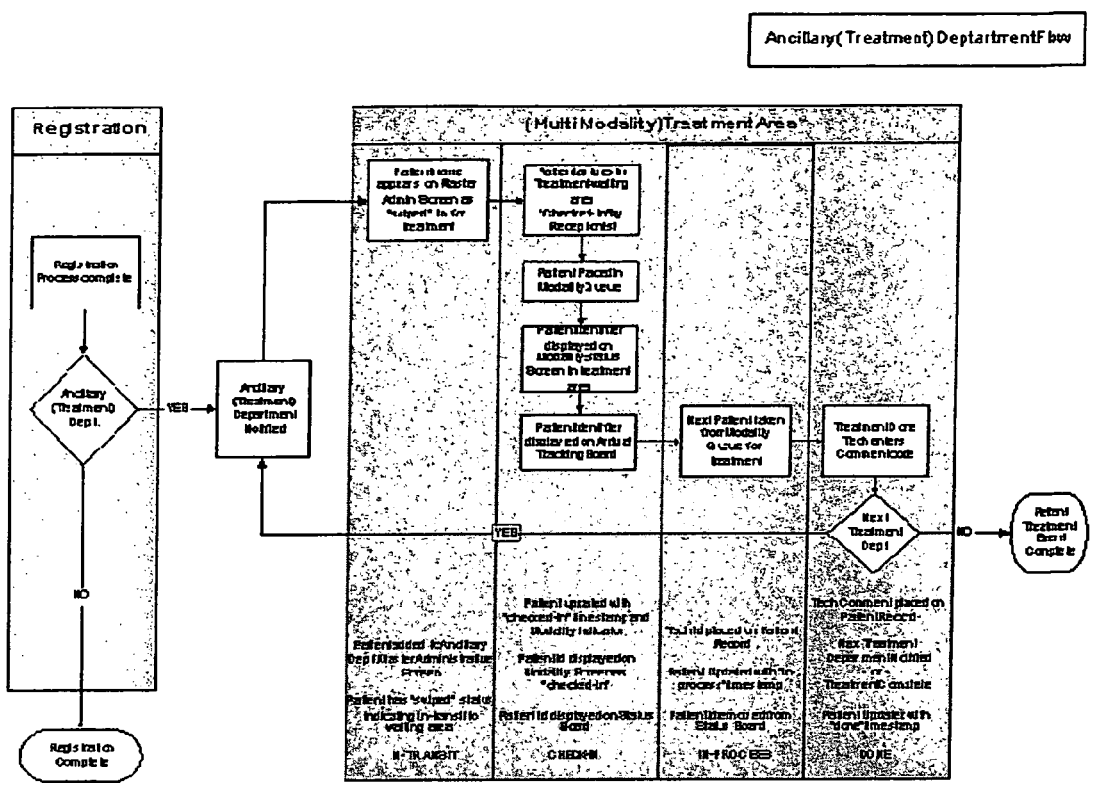
Figure 5:
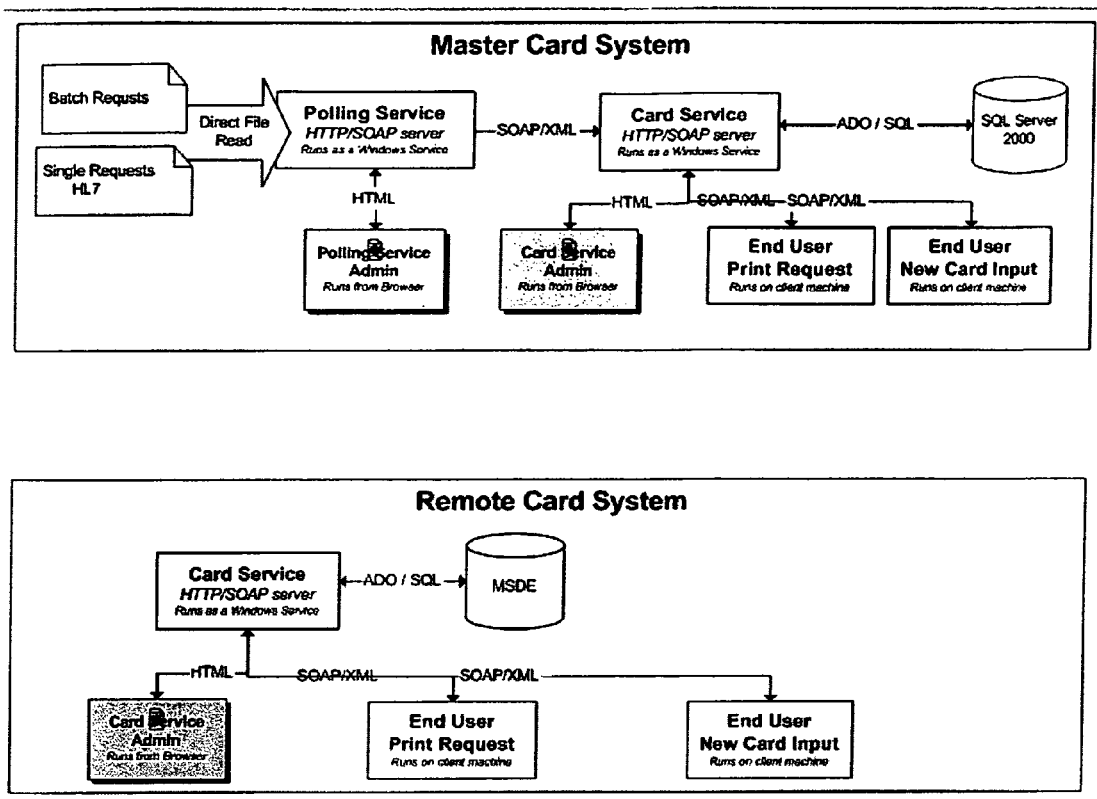
FIG. 5 is a pair of diagrams showing master card and remote card systems.

Describing one embodiment of the system of the invention, the integration of the system of the invention into the registration business process flow of the healthcare facility is illustrated in FIGS. 3-5. As shown in FIG. 3, the patient has the option to check-in to the registration process using a Patient Identification Card (e.g., Loyalty Card) either at a check-in kiosk in the registration waiting area, or at the registration reception desk. The patient is asked to swipe his or her card, and then is instructed to electronically sign-in to complete the check-in process. If the patient does not have an identification card, the patient's name is entered into the system and the patient is requested to sign-in to complete the check-in process. Patients that do not have an identification card can receive one as part of the registration process for use on their next visit. Once the process is completed for either scenario above, the patient's name is placed in the registration queue for registration processing and a patient identifier is placed on a tracking board in the waiting area. For example, if the patient is registering for a radiological exam, upon completion of the registration process, notification is automatically sent to the radiology waiting area that registration has been completed, and the patient is listed in "swiped" status on the Radiology Status screen. When the patient reaches the radiology waiting area and presents himself for check-in, the patient identifier gets placed on a tracking board in the radiology waiting area, as depicted in FIG. 4.

If the patient is registering for an appointment with another ancillary department, upon completion of the registration process, notification is automatically sent to that ancillary department that registration has been completed, and the patient is listed in "swiped" status on that ancillary department's tracking screen. When the patient reaches that ancillary department waiting area and presents himself for check-in, the patient identifier gets placed on a tracking board in that department's waiting area.

Typically, the marketing services application uses a Services Oriented Architecture. The services are using a stand-alone HTTP server and communication via SOAP/XML interfaces (FIG. 5). Preferably, only the Card Service module talks with the database and all other applications (including the Polling Service) communicate with the Card Service module. In some embodiments of the invention, the marketing services application HL7 Interface is Level 2.2 using TCP/IP protocol.

In various embodiments of the invention, the system server software runs on Microsoft Windows 2000 Server or Windows 2003 Server platforms utilizing Microsoft SQL 2000 Server. System client software typically runs on Microsoft Windows 2000 Professional, Microsoft Windows XP Professional and Microsoft Windows XP Tablet Edition. The system software can be shipped with the following User Guides: System User Guide, Identification Card (e.g., Loyalty Card) System Installation Guide, Identification Card (e.g., Loyalty Card) System Remote Installation Guide, Identification Card (e.g., Loyalty Card) System Registration User Guide, Identification Card (e.g., Loyalty Card) System Remote System User Guide, and Identification Card (e.g., Loyalty Card) System Batch System User Guide.

EXAMPLE 3

Overview and Patient Flow of One Embodiment of the System

The Patient Tracking Application electronically checks-in a patient for registration, and then, upon completion of the registration process, notifies the receiving treatment department and tracks patient progress as patients move through the patient care event. The two queuing processes for registering and treatment are linked. By linking these two processes, patients who are going to many departments during a given visit have their waiting lines for either registration or treatment connected during their entire visit.

Within the check-in process, the system has four primary components: a) a check-in device that allows the patient to either check-in automatically using a Patient Identification Card, or manually if the patient does not have a card (e.g., this is a first time visit); b) a Patient Arrival Display Board identifying patients in an appropriately secure fashion; c) workstation-based administrative functions that allow the registrar to select patients for registration and notify the treatment department once registration processing has been completed; and d) electronically capturing and storing the patient's signature along with the date and time information, eliminating the requirement for a paper patient sign-in sheet. Upon completion of the registration process, the application notifies the receiving treatment department that the registration process is complete and that the patient is in-transit to that department, effectively setting them up automatically for check-in.

At the treatment department, the process resumes with the patient presenting himself to the department receptionist and checking-in to that department and modality (if applicable). The receptionist and treatment department personnel then process their patient queue similar to registration queue processing.

When treatment is complete, the treatment department can either close out the patient record or continue by notifying the next treatment department that the patient is in transit, and the process repeats.

Figure 6:
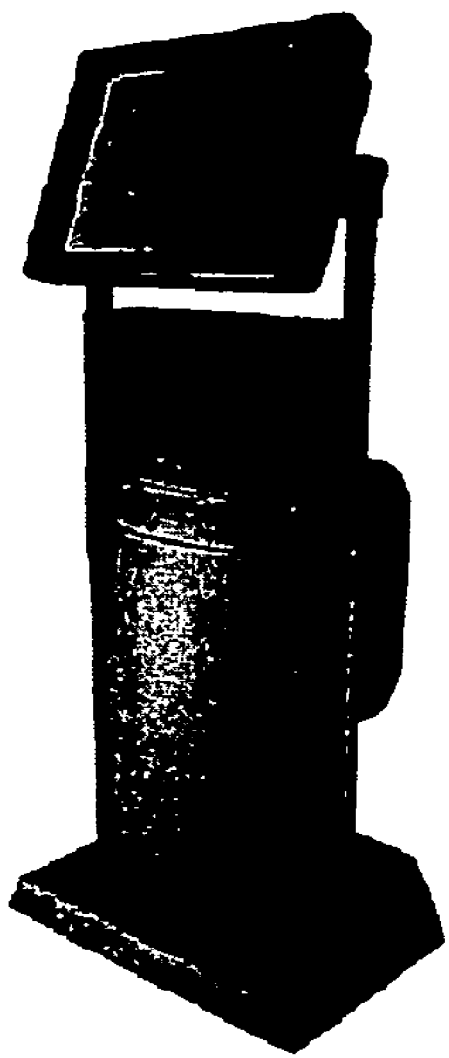
FIG. 6 is an illustration of a kiosk.
Figure 7:
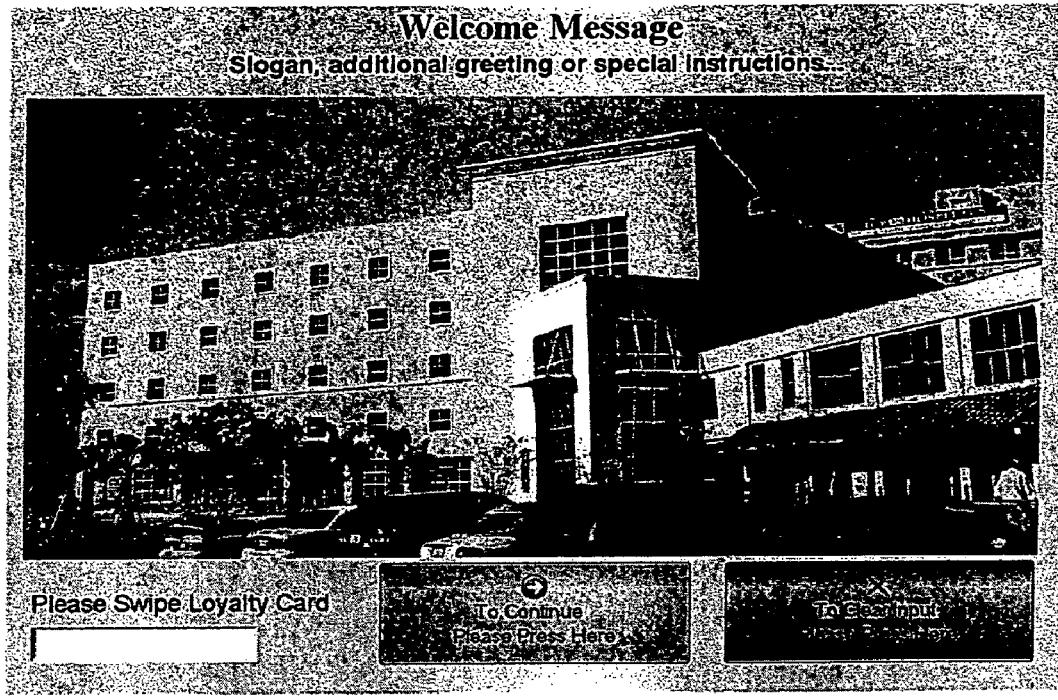

Patients with Patient Identification Cards are able to check-in to registration using their identification cards at kiosk stations, located near the entrances to the Outpatient Registration and Admission Departments. A kiosk main screen is shown in FIG. 6. In a typical registration process, the patient approaches the kiosk, where a Welcome screen (FIG. 7) is displayed. The patient swipes his or her identification card in front of the bar code reader. The identification card (e.g., Loyalty Card) number displays in the space provided below the "Please Swipe Identification Card" message. In the event that the kiosk is unable to read or recognize the Identification Card, the message: "Card ID not recognized Please go to the Desk for assistance" is displayed on the kiosk screen. The patient then presses either the Blue key to continue with the check-in process, or the Red key to cancel the check-in process, setting the kiosk for the next patient.

Figure 8:
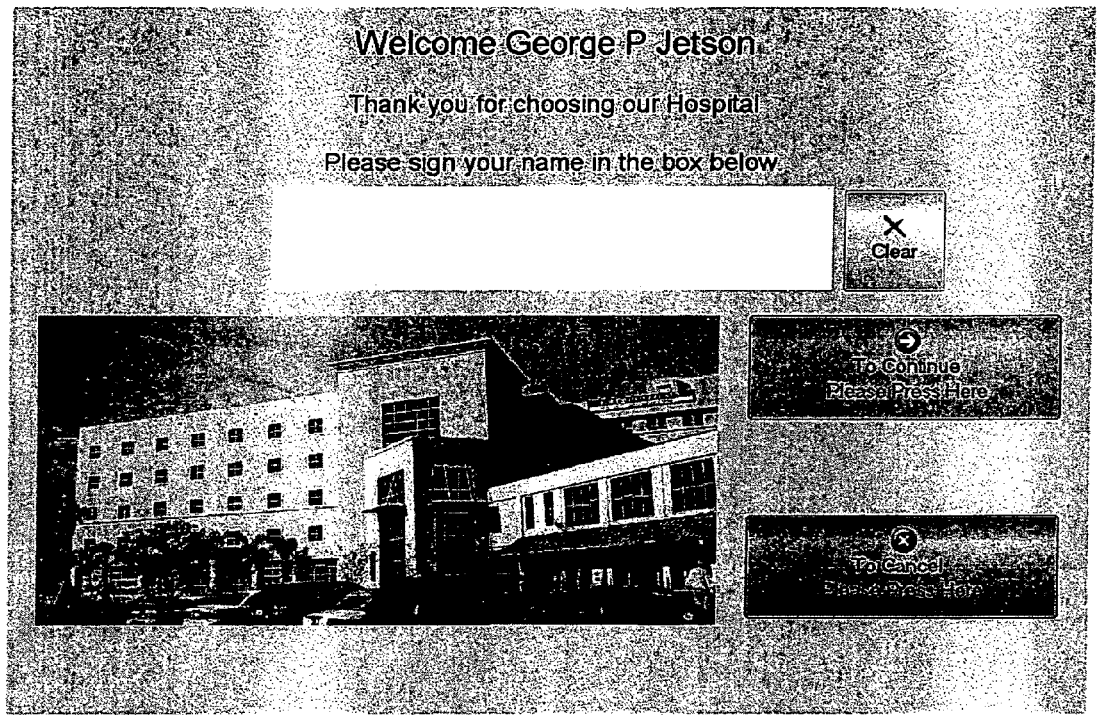

Upon pressing the Blue Continue Button on the Welcome screen (on the previous page), the patient Sign-In Screen (FIG. 8) is displayed on the kiosk. If the patient has a scheduled appointment, this screen also acknowledges the scheduled time of the appointment. If the patient is a walk-in without a scheduled appointment, the screen appears the same, without the line acknowledging the scheduled appointment time. The patient is instructed to electronically sign his name on the electronic sign-in interface. The patient presses the Blue button to continue the check-in process. Preferably, pressing continue without signing in presents a message to sign-in before proceeding. Pressing the Red Button cancels the check-in process and returns the patient to the main kiosk screen. Pressing the Clear button clears the signature pad and allows the patient to re-sign.

Figure 9:
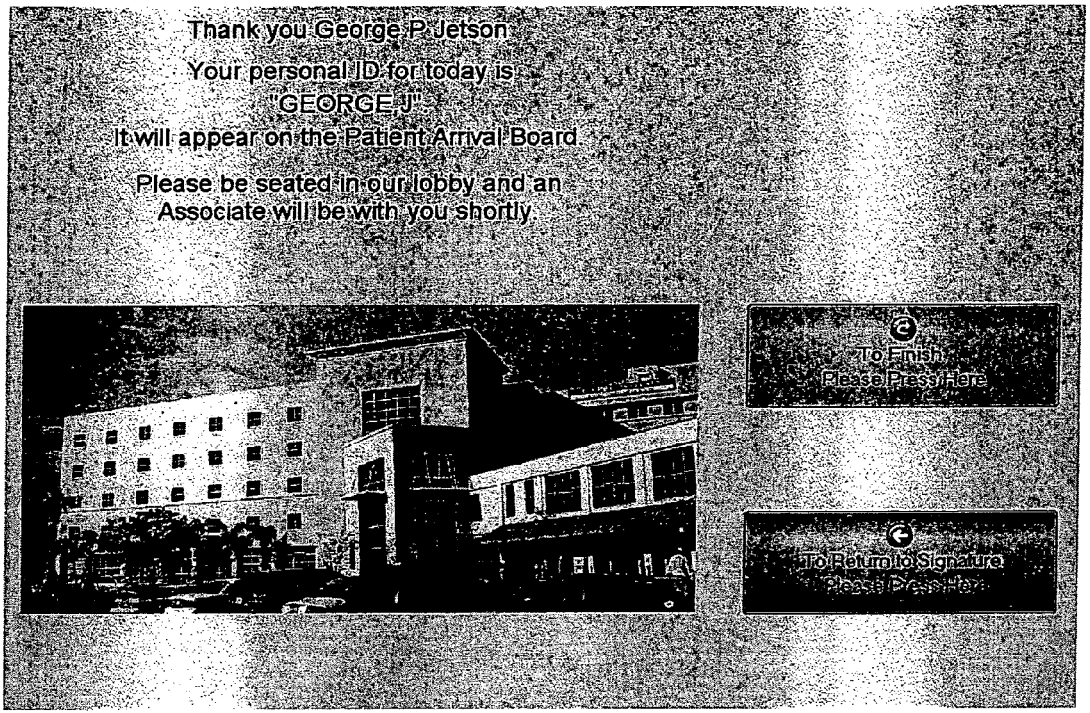

Upon pressing the Blue continue button on the Sign-In Screen, a Check-In Confirmation Screen (FIG. 9) message is displayed indicating the patient identifier that is displayed on the Patient Arrival Board for patient reference and instructing the patient to have a seat in the waiting area and wait to be called by a registrar. Pressing the Red Return button returns to the Signature Screen with a blank signature space to either re-sign, or to cancel the check-in while pressing the Blue Finish button on the Confirmation Screen clears this screen and presents the Welcome Screen (FIG. 7) for the next patient.

Figure 10:
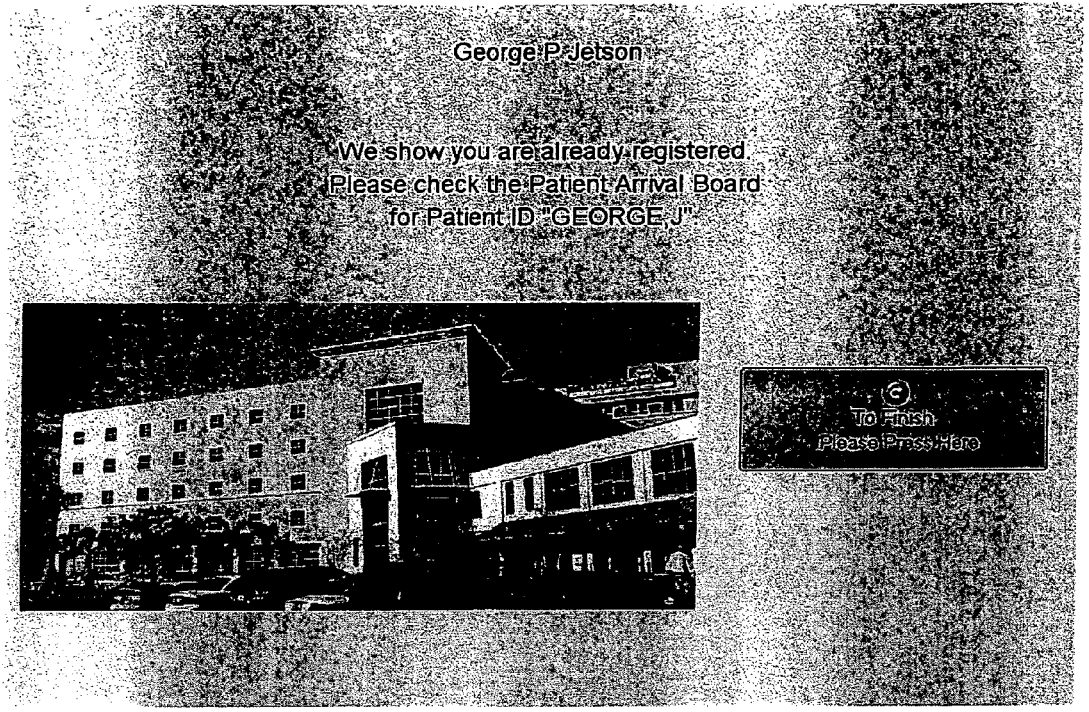

If a patient that has already checked-in swipes an identification card for a second time, the Duplicate Check-In screen (FIG. 10) is displayed indicating that the patient has already checked-in, and presenting a reminder of the patient's screen identifier as it appears on the Patient Arrival Screen. If a patient has checked-in, but does not remember his or her patient identifier, having them re-swipe their card presents this screen and the Identifier information. Pressing the Blue Finish button clears this screen and presents the Welcome Screen for the next patient.

Figure 11:
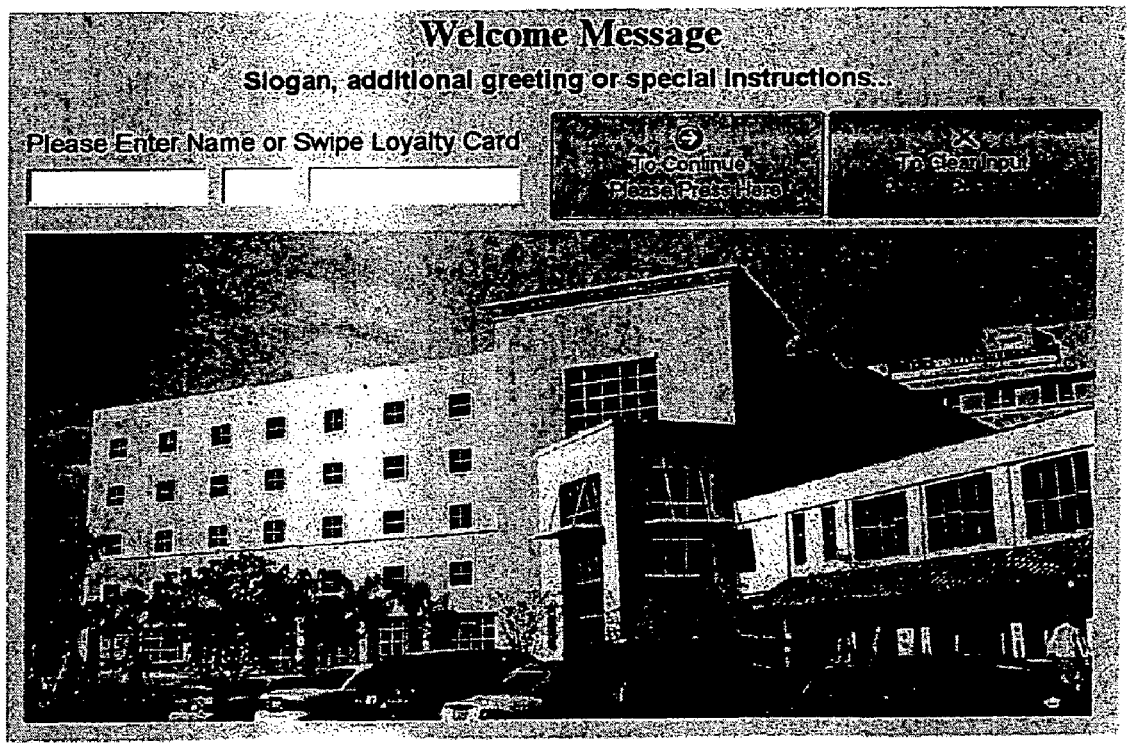

In order to accommodate patients who may not have a Patient Identification Card, or where they may have forgotten their card, Sign-in Tablet (PC's) have been set up with the registration receptionist. These tablets maintain the same swipe functionality for patients with Patient Identification Cards as the kiosks. Additionally, these tablets also provide the ability for the receptionist to type in the patient's name on a virtual keyboard and then have the patient sign-in electronically. An example of a Tablet main screen is shown in FIG. 11. If the patient approaches the Receptionist Counter with a Patient Identification Card, the patient swipes the card, and the number is displayed in the space provided. If the patient does not have a Patient Identification Card, the Receptionist types in the patient's name, using the keyboard attached to the tablet, and has the patient verify the spelling. The patient then presses either the Blue button to continue the check-in process, or the Red button to cancel the check-in process. From this point forward the process is the same as if the patient was checking in at a kiosk, a patient with a scheduled appointment is confirmed as above, and the patient is requested to electronically sign-in and press continue.

Figure 12:

Upon pressing the Blue Continue Button on the Tablet Welcome Screen, the patient Sign-In Screen (FIG. 12) is displayed. If the patient has a scheduled appointment, this screen also acknowledges the scheduled time of the appointment. If this is a walk-in patient without a scheduled appointment, the screen appears to be the same, without the line acknowledging the scheduled appointment time. The patient is also instructed to electronically sign-in their name on the electronic sign-in interface. Pressing the Blue button continues the check-in process. Preferably, pressing continue without signing in presents a message to sign-in before proceeding. Pressing the Red Button cancels the check-in process and returns the patient to the main kiosk screen. Pressing the Clear button clears the signature pad and allows the patient to re-sign.

Figure 13:
Figure 13:
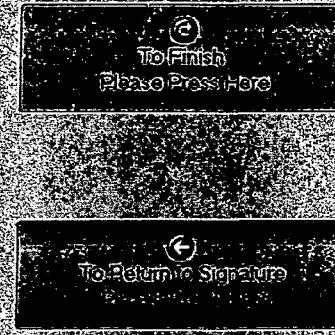

Upon pressing the Blue continue button on the Sign-In Screen (on the previous page), the Check-In Confirmation Screen message shown in FIG. 13 is displayed. This screen indicates the patient identifier that is displayed on the Patient Arrival Board for patient reference and instructs the patient to have a seat in the waiting room and wait to be called by a registrar. Pressing the Red button returns to the Signature Screen with a blank signature space to either re-sign, or to cancel the check-in. Pressing the Blue Finish button clears this screen and presents the main kiosk screen for the next patient.

Figure 14:
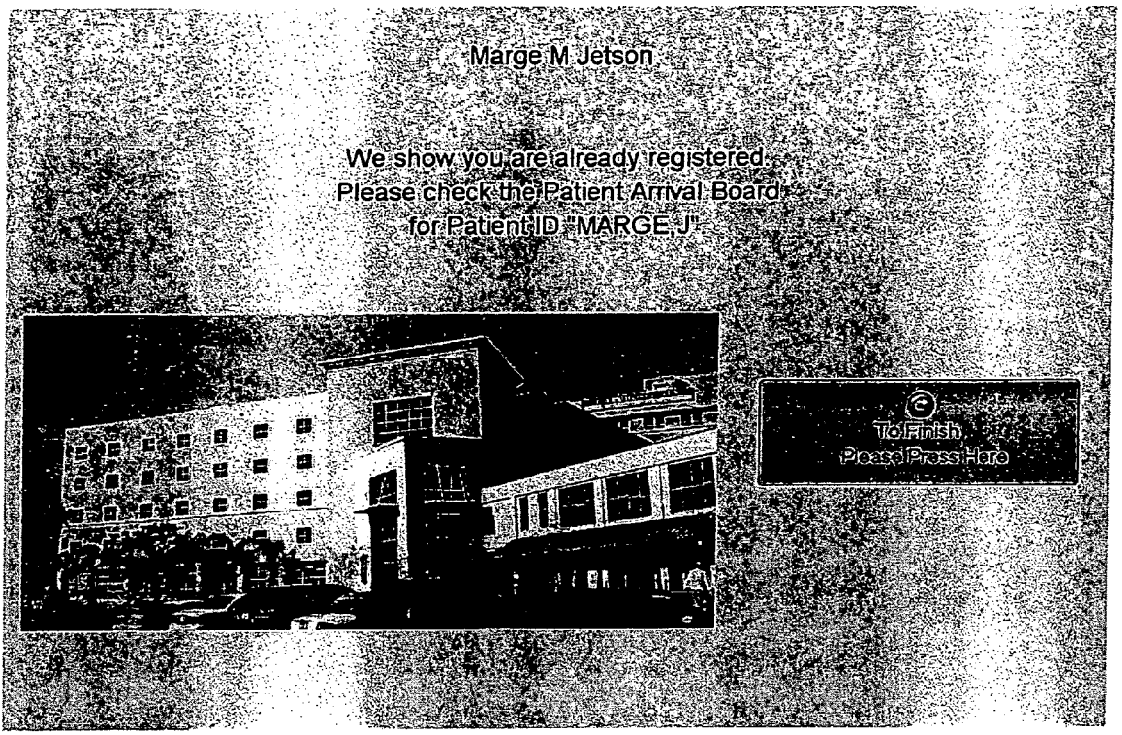

If a patient that has already checked-in swipes a Loyalty Card for a second time, the Duplicate Check-In screen (FIG. 14) is displayed, indicating that the patient has already checked-in, and presenting a reminder of the patient's screen identifier as it appears on the Patient Arrival Screen. If a patient has checked-in, but does not remember his or her patient identifier, having them re-swipe their card presents this screen and the Identifier information. Pressing the Blue Finish button clears this screen and presents the main kiosk screen for the next patient.

The system features patient tracking application functions. The Master Administrative Screen is used to track and process the patient through both the registration and/or ancillary treatment department processes. Both versions of the Master Administrative Screen process the same way with some additional functionality that has been enabled for the ancillary treatment departments to allow for local patient check-in to the ancillary treatment department and modality queue. The functionality for the registration department is explained in the next section.

Figure 15:
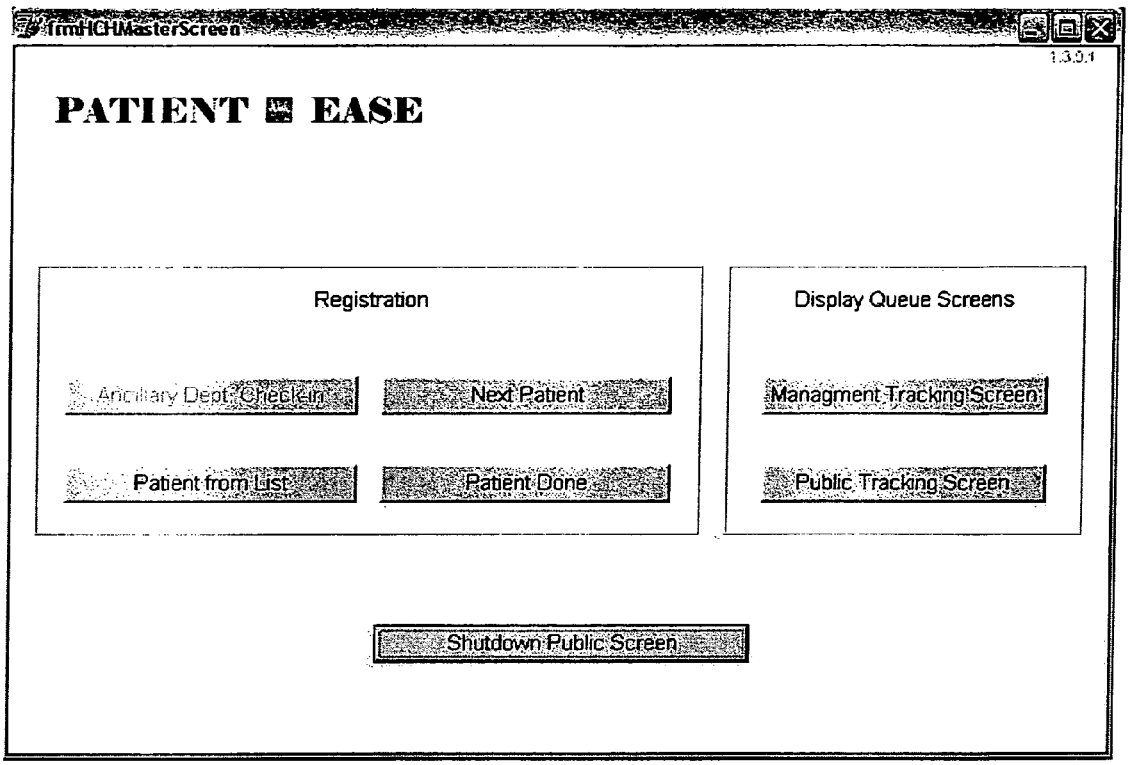
Figure 16:
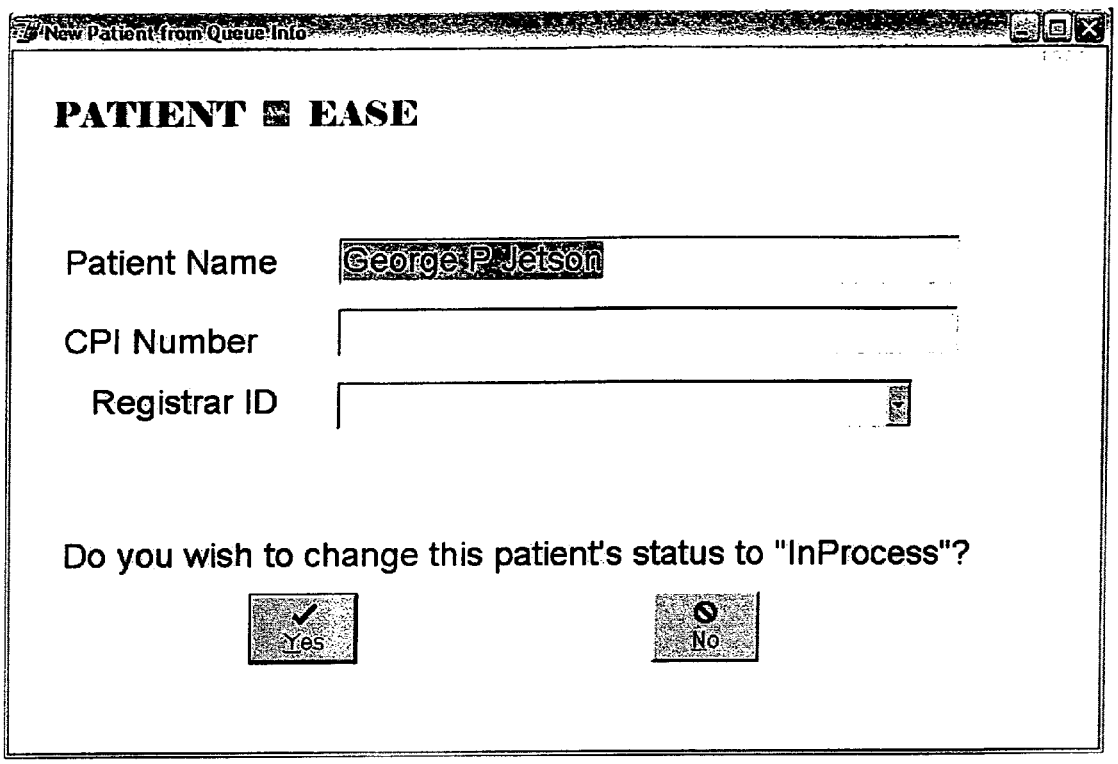

The Registration—Master Administrative Screen (FIG. 15) displays on the Registration Reception Desk Workstation for the receptionist or registrar to "work" the patient through check-in and registration, forward the patient to the treatment department, correct mistakes, and perform utility functions within the application. Once a patient has checked-in to registration via the kiosk or tablet functions, the patient is now in the Patient Tracking Application and is processed using the screen functions shown beginning in FIG. 16.

The registrar (or receptionist) presses the NEXT PATIENT button on the Registration side of the Master Administrative Screen. The next patient in the Queue for Registration Processing screen (FIG. 16) is displayed. Upon identifying the patient in the waiting area, the registrar selects his or her ID from the dropdown list of registrars and presses the YES button. The patient name is removed from the Patient Arrival Board, and the patient status is changed to "in process" in the system. Selecting NO returns the receptionist to the Master Administrative Screen. In some instances, the next sequential patient may not be ready or available for the registration. In these cases, the Patient From List button is used to select the next patient.

Figure 17:
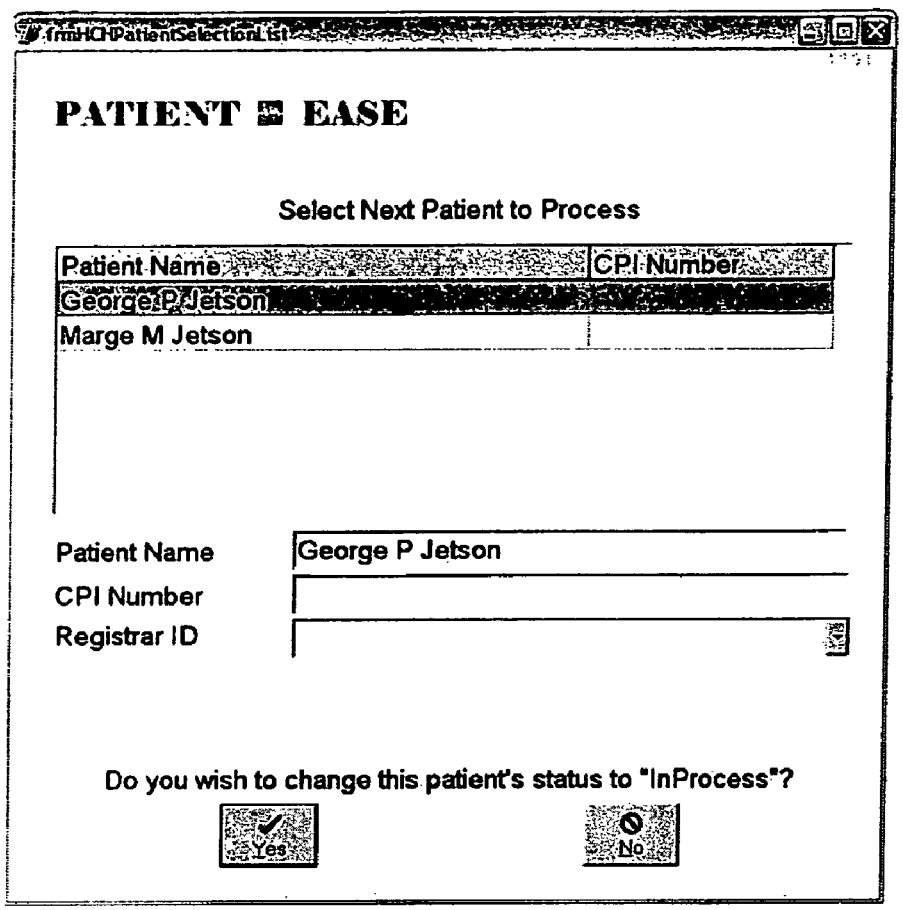
Figure 18:
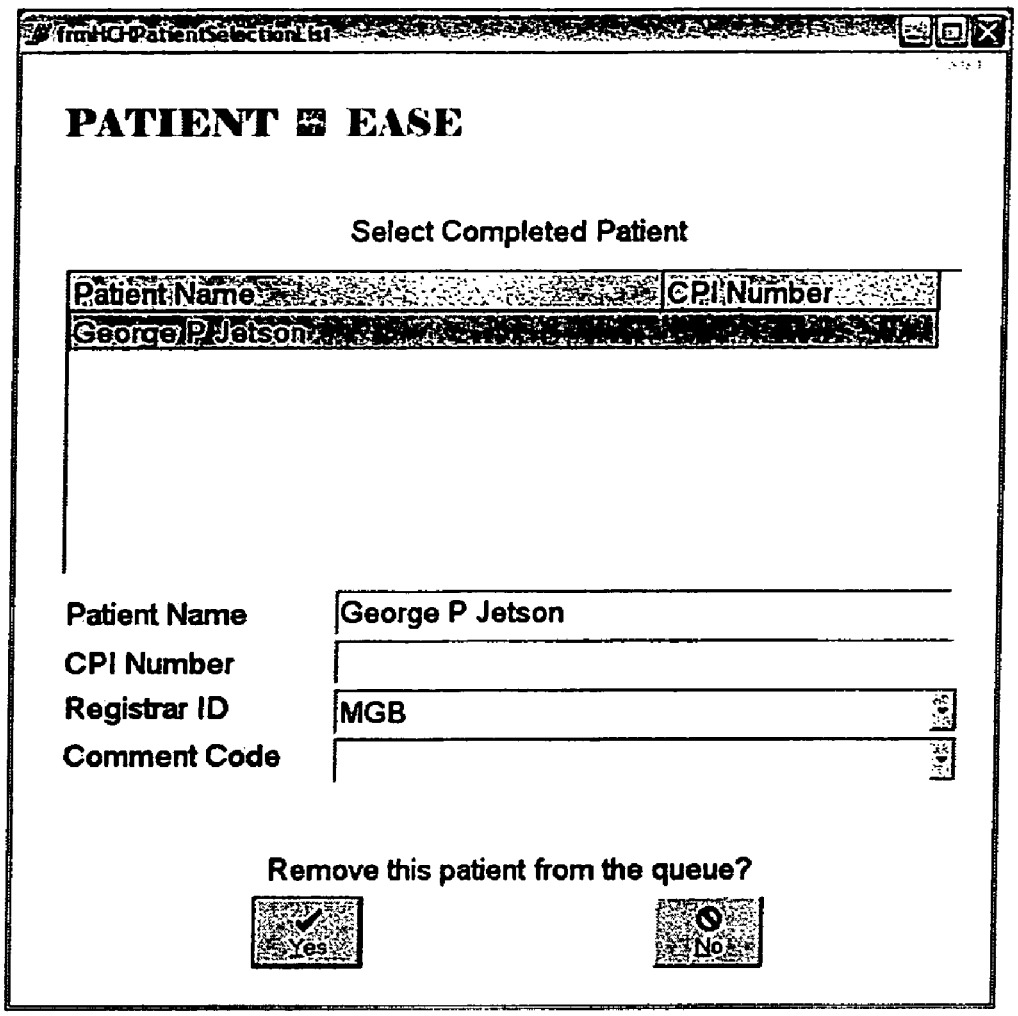
Figure 19:
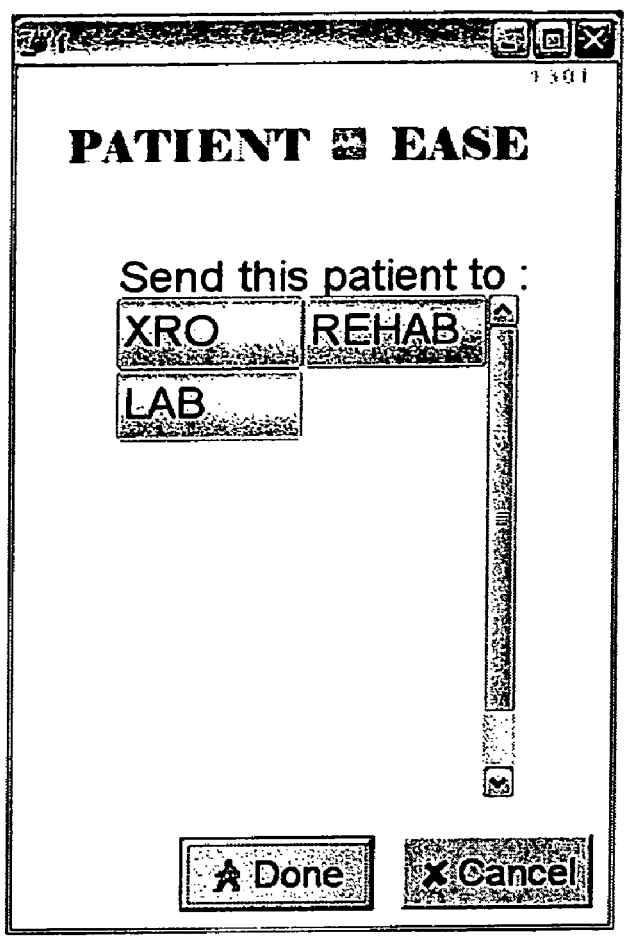

The registrar (or receptionist) presses the PATIENT FROM LIST button on the Registration side of the Master Administrative Screen which then displays a selection list (FIG. 17) of all "in-process" patients for the registrar to choose from. Highlighting the patient moves the patient down to the confirmation area. Upon identifying the patient in the waiting room, the registrar selects his or her ID from the dropdown list of registrars and presses the YES button. Pressing YES removes the patient name from the Patient Arrival Board, and the patient status is changed to "in process" in the system. Selecting NO returns the receptionist to the Master Administrative Screen. The registrar (or receptionist) presses the PATIENT DONE button on the Registration side of the Master Administrative Screen. This screen (FIG. 18) displays a selection list of all "in-process" patients for the registrar to choose from. Highlighting the patient moves the patient down to the confirmation area, where the registrar will: a) confirm the registrar ID—in case the registrar has changed, and b) enter a comment code for this patient registration if necessary. Pressing YES displays the Send To Department screen (FIG. 19). Selecting a department on this screen sends notification to the receiving department that the patient is on his or her way for treatment and sets the patient to "in transit" status on their master screen. If the Send To department is not displayed, then the "Done" button can be selected to change the patient status to completed. Pressing NO returns the registrar to the Master Administrative Screen and leaves the patient in in-process status.

Figure 20:
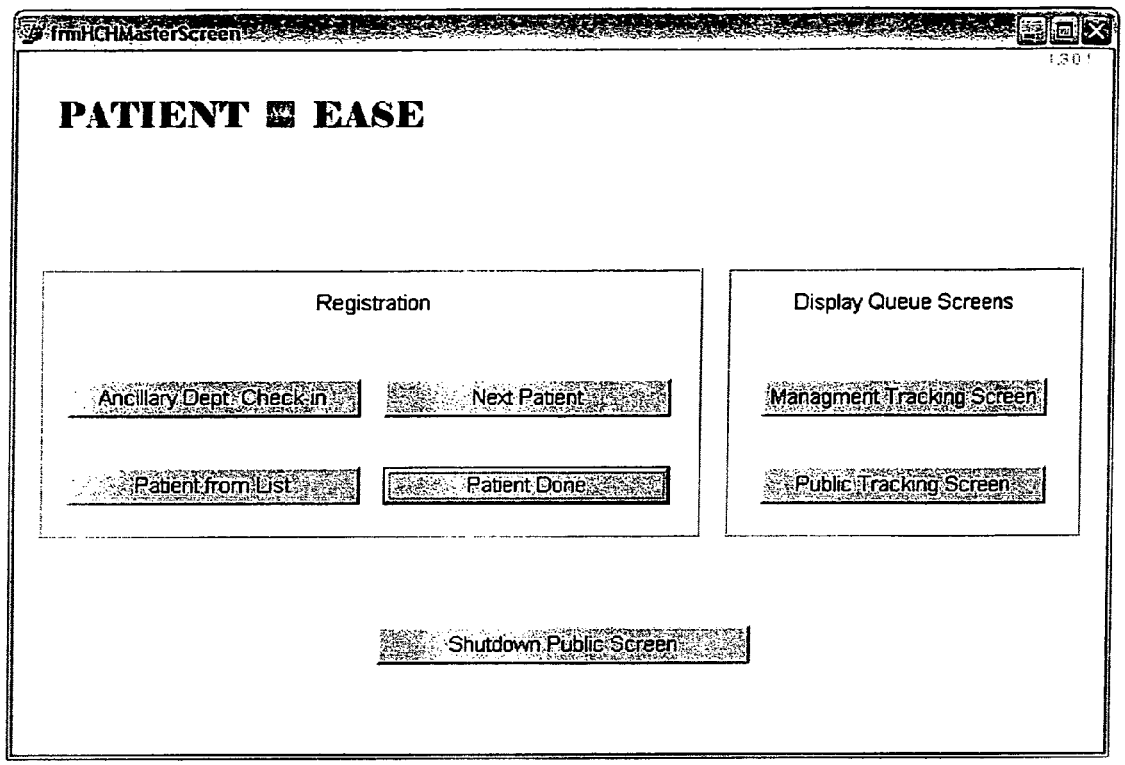

The Ancillary Treatment Department—Master Administrative Screen (FIG. 20) displays on the Ancillary Treatment Departments Reception Desk Workstation for the Receptionist or Tech to "work" the Patient Check-in Queue, correct mistakes, and perform utility functions within the application. Upon presenting himself at the Treatment Department waiting area, the Receptionist presses the ANCILLARY DEPT. CHECK-IN button on the Treatment Department side of the Master Administrative Screen. A List of patients that are "in-transit" from registration or another treatment department is displayed for selection. Upon identifying the patient, the receptionist performs the following steps: selects his or her ID from the Dropdown list of Ancillary staff, and assigns the patient to a Modality Queue if applicable from the dropdown list of available modalities for that treatment department. Pressing YES moves the patient from "in-transit" (swiped) status to Checked-in within the Department and Modality. The patient name is added to the Patient Arrival Board, and the patient record is updated as "Checked-in" in the system. The patient name is also displayed on the Queue-View Screen for the Department (or modality) as checked-in and awaiting treatment. Selecting NO returns the Receptionist to the Master Administrative Screen with no change to the patient tracking record.

If the department processes its patients on a first in-first out basis, the Next Patient function is used. This typically is not for departments where multiple modalities exist. The receptionist or tech presses the NEXT PATIENT button on the Treatment Department side of the Master Administrative Screen and the next checked-in patient for Treatment is displayed. Upon identifying the patient in the waiting room, the tech selects his or her ID from the Dropdown list of Techs (to update the field). The Modality (if applicable) is verified and updated if necessary. Pressing YES updates the patient tracking record with the new information, and moves the patient to in-process status in the tracking application. The patient name is removed from the Patient Arrival Board, and the patient status is changed to "in treatment" in the system. Selecting NO returns the receptionist to the Master Administrative Screen.

In multiple modality departments, and for some instances where the next sequential patient may not be ready or available for treatment, the Select Next Patient from List button is used to select the next patient from the list of available patients. The receptionist or tech presses the PATIENT FROM LIST button on the Treatment side of the Master Administrative Screen which displays a selection list of all "Checked-in" patients for the registrar to choose from. Highlighting the patient moves the patient down to the confirmation area where Modality Queue is displayed for that patient. Upon identifying the desired patient in the waiting room, the tech selects his or her ID from the Dropdown list of Techs (to update the field). The Modality (if applicable) is verified and updated if necessary. Pressing YES updates the patient tracking record with the new information, and moves the patient to in-process status in the tracking application. The patient name is removed from the Patient Arrival Board, and the patient status is changed to "in process" in the system. Selecting NO returns the receptionist to the Master Administrative Screen.

Once patient treatment is complete, the receptionist or tech presses the PATIENT DONE button on the Treatment side of the Master Administrative Screen which displays a selection list of all "in-process" patients for the registrar to choose from. Highlighting the patient moves the patient down to the confirmation area where Modality Queue is displayed for that patient. Upon identifying the desired patient to complete treatment, the tech confirms his or her ID from the Dropdown list of Techs and updates the field as necessary. The Modality (if applicable) is verified and updated if necessary and a Comment Code is selected from the dropdown list of available codes if necessary. Pressing YES displays the Send To Department Screen. Selecting the next treatment department on this screen sends notification to the receiving department that the patient is on his way for treatment and sets the patient to "in transit" status on their master screen. Since the relationship between departments and modalities has been established and maintained in the Queue Table, the user is presented only with the associated treatment departments to select from. If there is a treatment department which does not allow subsequent routing, the screen shows the message on the right. If DONE is selected, the patient is marked as complete for the patient's treatment event, and no forwarding notification records are created. Selecting CANCEL from the Send To Department Screen returns the Receptionist to the Master Administrative Screen and the patient record remains in "in-process" status.

Figure 21:
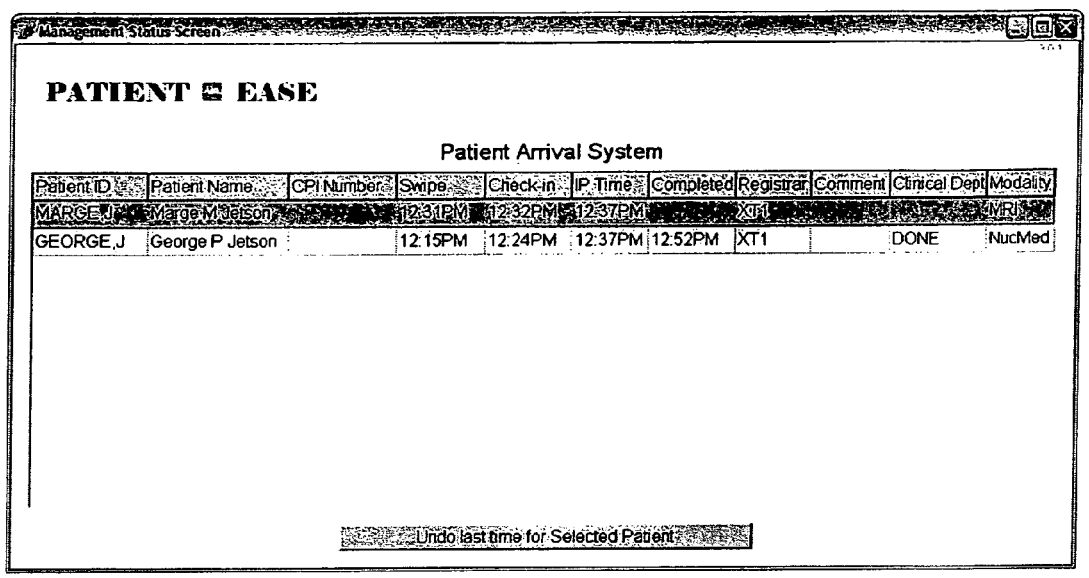

Selecting the MANAGEMENT TRACKING SCREEN button on the Display Queue Screens side of the Master Administrative Screen results in the display shown in FIG. 21. This screen functions the same in both Registration and Ancillary Treatment Department Modes, and displays all of the patients in that specific queue for the day and their status or disposition from the check-in queue. This Screen is similar to the QueueView™ (Incoming Calls Management Institute, Annapolis, Md.) screen that is available to registrars and treatment department staff to view patient activities and to complete (DONE) patients in the system remotely. Additional functionality is provided in the Master Administrative Screen to allow the user to view and "UNDO" entries performed in error. For example, an incorrect patient is selected and processed as DONE in error. The UNDO button can reverse the last timestamp for that patient (as explained below). The Management Status Screen displays the list of all patients and their status within the Registration or Treatment Departments. The Modality and (Next) Clinical Department columns are populated as appropriate for the department or registration area. Patients that have been checked-in but not processed for a specified elapsed time are indicated with a YELLOW status color based on a setting in the workstations ".ini" file that has determined according to a pre-determined user defined business rule. If that patient wait time exceeds a maximum wait time, the status color changes to RED and an e-mail notification is sent to a supervisor for resolution and follow-up based on a setting in the workstations ".ini" file that has determined according to a pre-determined user defined business rule. Highlighting a patient and pressing the UNDO LAST TIME FOR SELECTED PATIENT removes the most recent timestamp from the patient record. The Patient record is re-set to the previous status. A warning window appears asking "Are you SURE you want to change the Patient Status?" Selecting YES completes this transaction. Selecting NO returns the user to the Master Administrative Screen. Repeating this process removes the status of the record completely provided the patient has not been forwarded to, and checked-in by, the "sent to" department. All Undo activities are preferably logged to an audit table for review in case of errors or discrepancies.

Selecting PUBLIC TRACKING SCREEN from the Master Administrative Screen results in a display that appears on the Patient Arrival display. The information is publicly viewable in the Registration and Treatment Department waiting areas. Selecting PUBLIC TRACKING SCREEN from the Display Queue screens section of the Master Administrative Screen displays the Patient Arrival Board (FIG. 22) on the display board (which is preferably large) in the waiting area. Selecting SHUTDOWN PUBLIC SCREEN from the Master Administrative Screen shuts down the Patient Arrival Tracking board. A warning window appears asking "Are you SURE you want to shutdown the PUBLIC Tracking Screen?"

EXAMPLE 4

Use of QueueView™

The QueueView™ Application is an application that resides on any PC as a "remote" view of the Management Status Screen for the selected department or Modality. This application may also reside in a Citrix environment. QueueView™ has been designed to provide an Inquiry function to provide a detailed view of patient tracking information as well as a Process function to enable specific patients to have a completed status of "Done." This capability is controlled via a setting in the workstation's ".ini" file. QueueView™ is deployed in two configurations: a) Administrative view—for supervisors to monitor activity with no ability to change or alter patient tracking information; and b) Registration/Clinical Department View—providing the user with the ability to view patient activity for the specified department or queue with additional functionality to allow these staff to complete (DONE) a patient from their work area. Status notifications are processed in QueueView™ the same as for the Management Status Screen in the Master Administrative Screens.

Figure 23A:
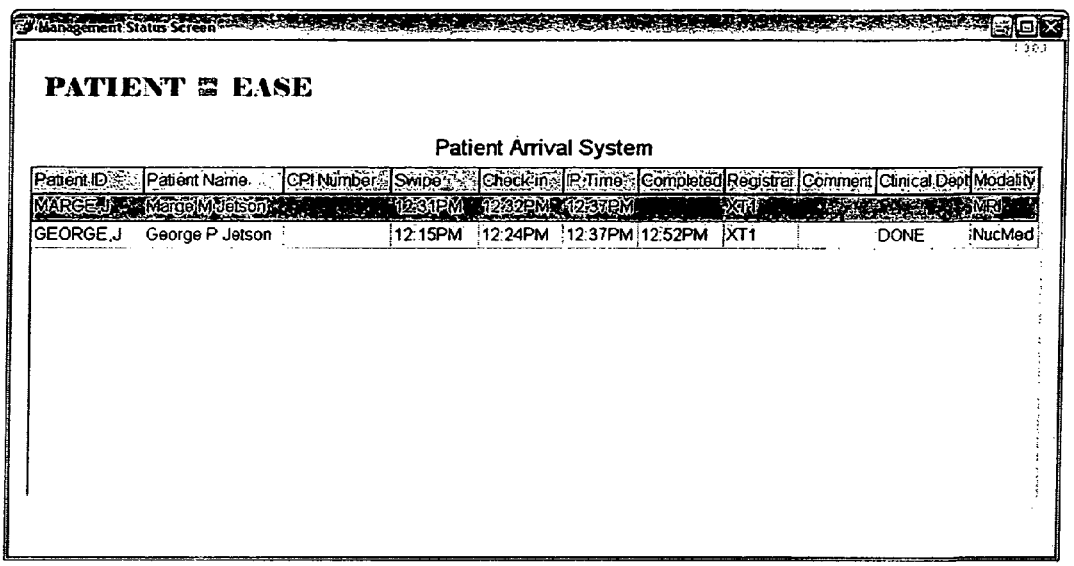
Figure 23B:
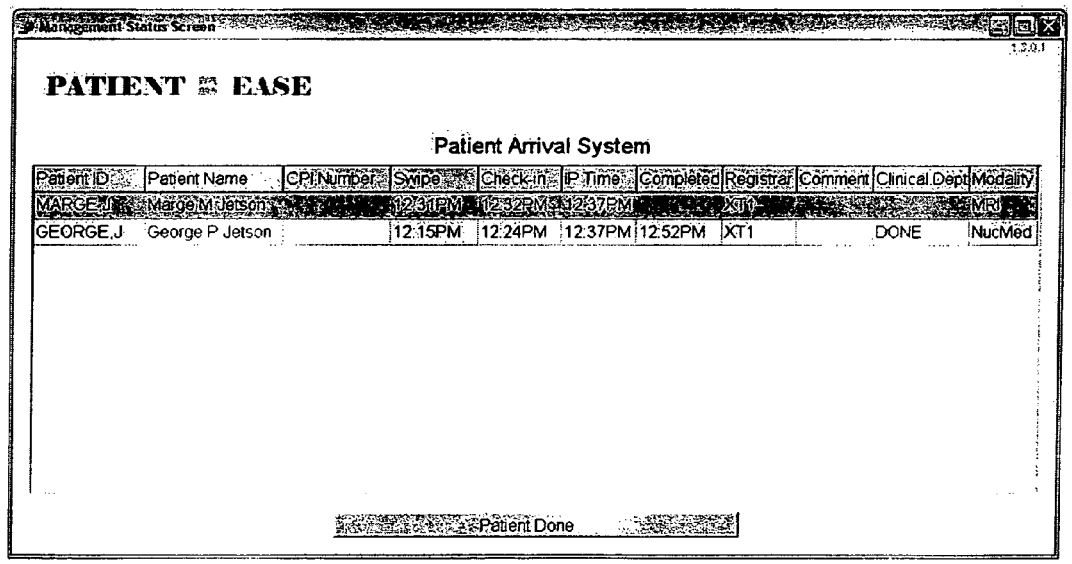

The Administrative View screen (FIG. 23A) allows the supervisor or department head to view activity in the system without going to the reception desk to view the Management Status Screen. The Registration/Clinical Department View screen (FIG. 23B) allows the registrars, department clinicians, and techs to view activity for their department or modality remotely in their work areas to monitor patients that are waiting to be processed. The DONE button on this screen functions the same as the Registration or Ancillary Treatment DONE buttons, depending on where the application is used.

Figure 24:
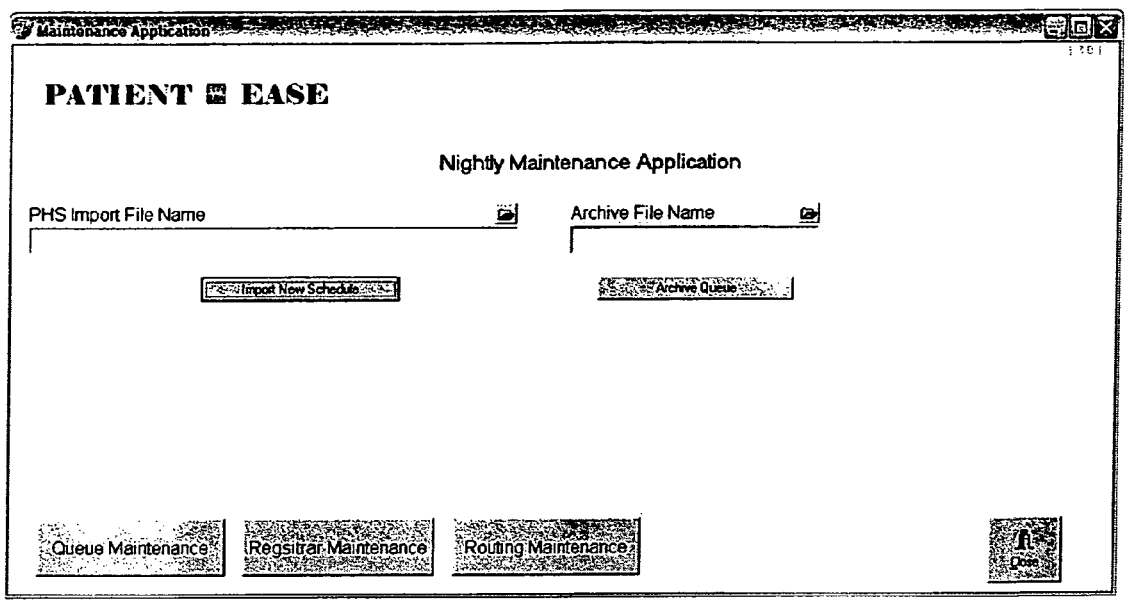

The Maintenance Application Functions screen (FIG. 24) is for loading the Daily hospital scheduling system file, archiving Daily Activity to the History File and generating the Signature report file, loading Identification Card (e.g., Loyalty Card) Information, Reference Table Upkeep, Department and Modality Queue Maintenance, Routing Maintenance, and Registrar and Comment Maintenance. These functions are not for use by the general user population but are used to maintain certain components of the application environment and to load reference data and tables. To import the Daily Schedule information for the next business day, enter the path and file name for the schedule to be imported if it does not automatically populate the Import File Name and Press Import New Schedule. A display indicates the number of scheduled records loaded. To Archive the daily activity and Electronic Signatures at the end of the day, press the Archive button. The Archival Signature report for all departments and queues is generated and saved to the Database Server. All Daily Transactions are moved to the Patient Activity History table for reference and reporting availability. To Import/Update Loyalty Card information, enter the path and file name for the Loyalty Card load file (.CSV format) and press the Import/Update Button. A display indicates the number of records processed.

Figure 25A:
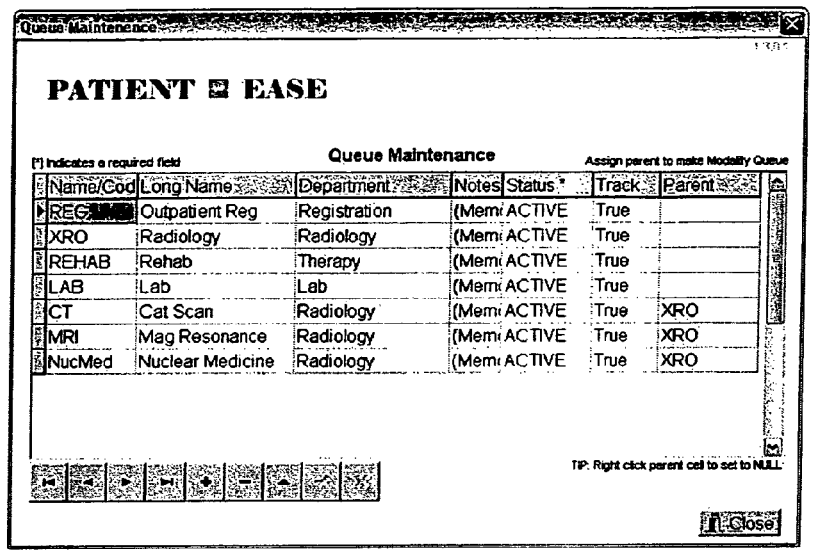
Figure 25B:
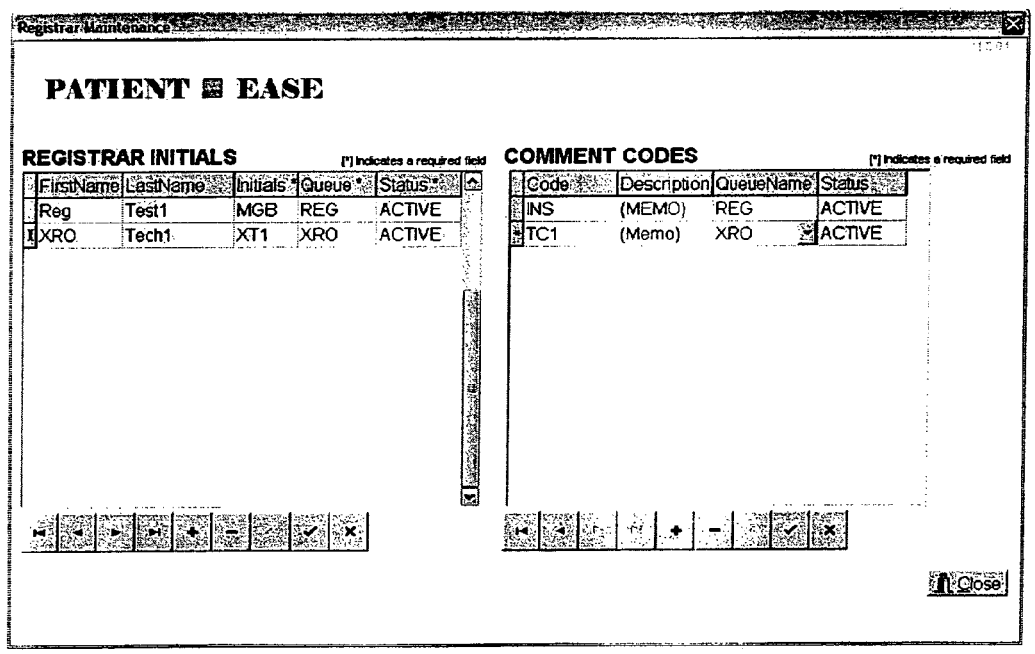

The Queue Table Maintenance Screen (FIG. 25A) is used to add and de-activate department and modality queues within the Patient Tracking Application. Queues can be either department queues or modality queues depending on whether a parent queue is indicated in the Parent column. This is used for aggregating modalities within a department for screen displays and reporting. Field Descriptions include: a) Name/Code*—the Queue Identifier which is displayed in all selection screens (this is also the entry that is used in the PatientArrivalTracking.ini file to configure the application to point to the appropriate queue or department); b) Long Name—descriptive name for the queue; c) Department—an optional field; d) Notes—memo area where specific information can be noted for a specific queue; e) Status*—indicates whether the queue is active or inactive (once a queue has been applied to a tracking record it can not be deleted, but can get marked as inactive to prevent further use); and f) Parent (where "child" modalities are assigned to "parent" departments). An asterisk (*) indicates required fields to update and add Department and Modality Queues to the database and application. To allow for hierarchical processing and future reporting, the Parent column is used to aggregate modalities to higher level departments The Registrar Initials table on the Registrar Maintenance screen (FIG. 25B) defines personnel to the application for assigning them to patient process activities and audit trail functions. These Personnel identifiers are specific to a particular department. If a resource works in multiple departments or areas, they will need to be entered in multiple times. The Comment Codes table defines the standardized comments that are used to add notations to patient records for reference and analytical purposes. These comments are Department or Modality specific. The Registrar Initials maintenance screen (FIG. 25B) is used to enter Registrar, Tech, and Receptionist initials and identifying information into the application for the ID functions on the Patient selection and Done functions (these ID's are Department Queue Specific). The Comment Code maintenance section of the Registrar Maintenance screen (FIG. 25B) is used to enter Comments and comment codes for the Done Screens throughout the application (these codes are preferably Department Queue specific).

Figure 26:
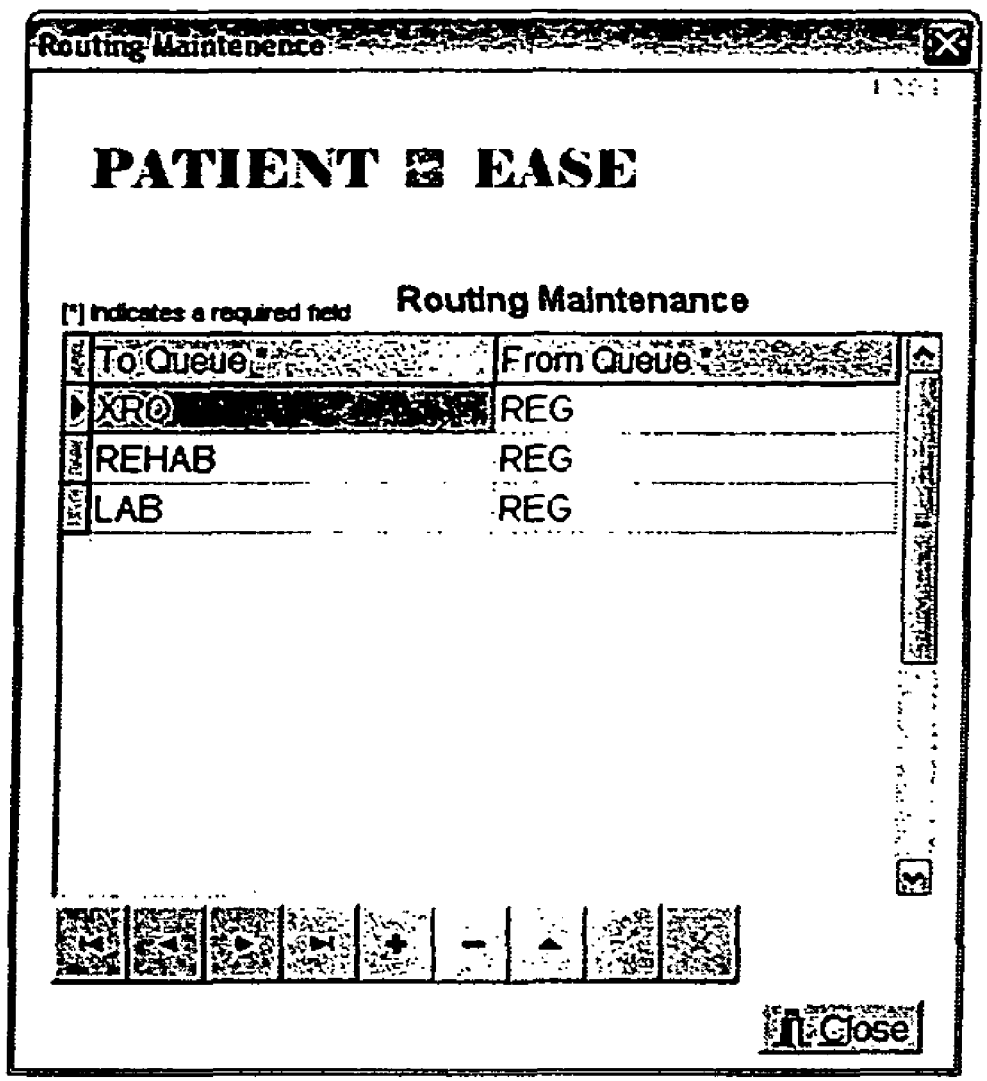

The Routing Maintenance Table screen (FIG. 26) is where the application maps target departments to source departments. This allows the user to define where one department can send patients upon completion (DONE Process) within that department. Mappings made in this table populate the "Send To" screen at the completion of a patient treatment event within a department. This table maintenance screen maintains the routing relationships for each department within the application for the SEND TO screen functions at the end of the DONE process. The "To Queue" field identifies the "target" queue for the send to function, and can be populated with any queue entered in Queue Maintenance. The "From Queue" field identifies the "source" queue that is sending the patient, and can be any queue that is identified in Queue Maintenance. A queue can send a patient to itself—re-routing a patient through the radiology department for a second modality treatment. The to and from relationships are meaningful and relevant so as not to populate the selection screen with incorrect or inaccurate information.

Figure 27A:
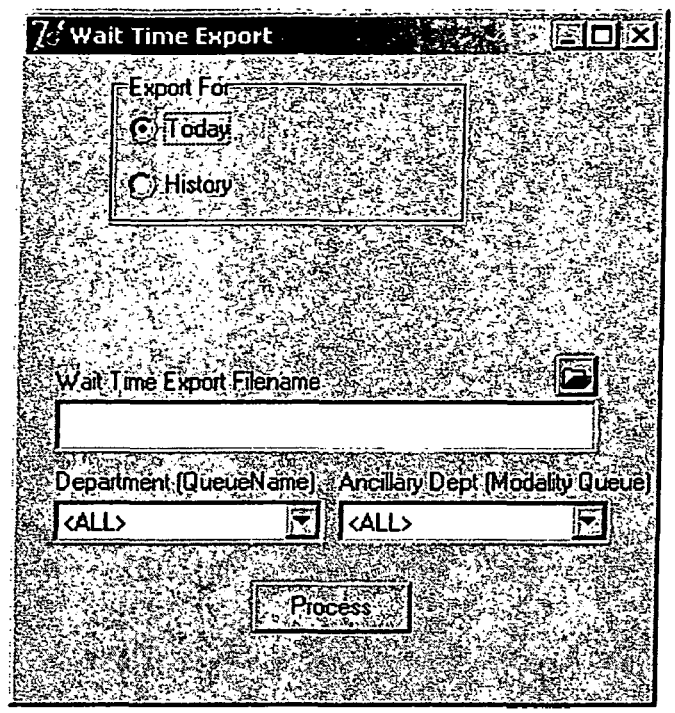
Figure 27B:
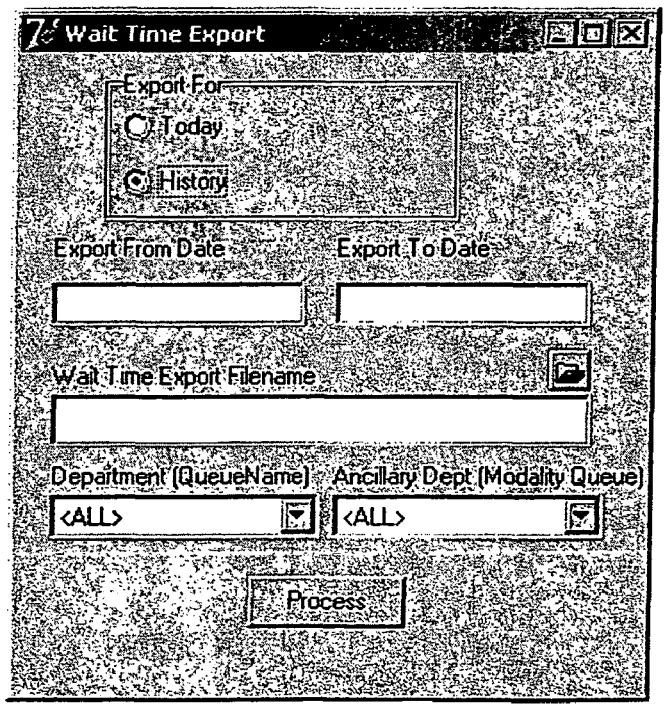

The system includes a Wait Time Export Function which provides an export of the patient tracking data into a format (e.g., comma delimited) suitable for use in a software program such as Microsoft Excel. This function allows for the export of the current day's data or data from one or more days of history. Clicking on the desktop icon labeled "Wait Time Export" results in the display of the screen shown in FIG. 27A. The screen displayed defaults to select data from 'Today.' Clicking on 'History' presents the screen shown in FIG. 27B.

Figure 28A:
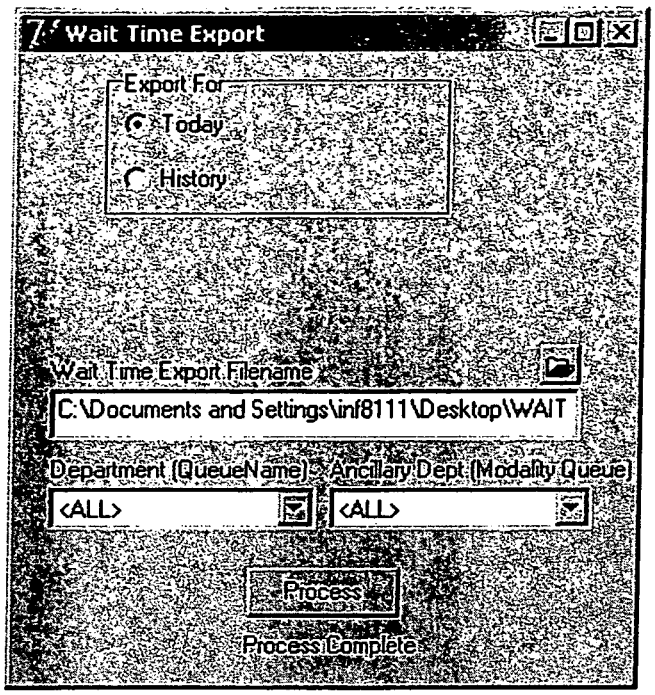
Figure 28B:
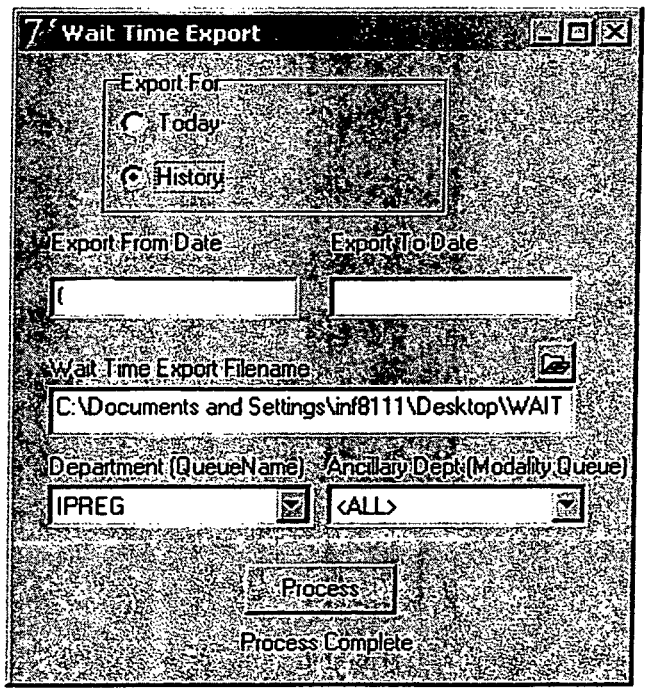

If an export of historical data is required, then the user clicks on 'History' and populate the 'Export From Date' and 'Export To Date' fields or retains the default selection of 'Today.' Clicking on the Folder Icon selects the filename and destination for the resulting export file. A dialog box: 'Save As' is displayed. Once the export function is complete, the screen shown in FIG. 28 is displayed for either current day or historical data. Close the 'Wait Time Export' dialog box by pressing the 'X' in the upper right hand corner of the display. There is an Icon on the desktop labeled 'Wait Time' which is the resulting CSV (Comma Separated Value) file created from the export function. Double clicking on this icon opens the file with Microsoft Excel if installed on the workstation.

EXAMPLE 5

GlobalView™ Dashboard

Figure 29A:
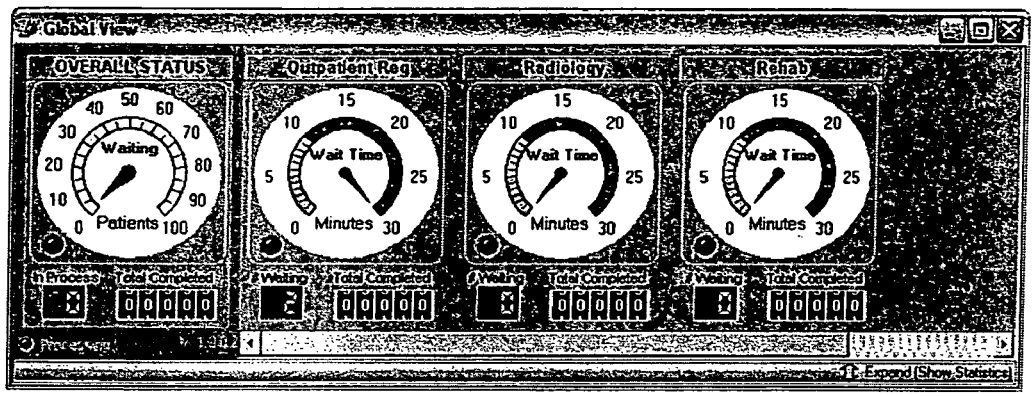

The GlobalView™ Dashboard inquiry function provides Administration and Customer Service with the ability to view in real time Patient Tracking activity for all Registration and Treatment Department Queues in which the Patient Tracking Application has been deployed. Double clicking on the 'Patient Tracking GlobalView' icon on the Windows desktop results in the display shown in FIG. 29A. An 'Overall Status' section describes cumulative information for all areas showing: on the meter the total number of patients waiting to be "serviced" (either registration or treatment); the current number of patients "in process" in the odometer gauge; and the total completed patients is displayed in its identified counter box. Adjacent sections represent each of the registration/treatment areas that the Patient Tracking Application has been deployed to throughout the facility. If the number of departments exceeds the screen limitations, a scroll bar displays so that one may scroll to view all departments. Each area depicts at a glance the summary status of patients in a respective Registration or Ancillary Department. Depending on the refresh rate that has been user-defined on this particular workstation, this display and the underlying statistical information is refreshed so as to reflect current data from the facility in real time.

Figure 29B:
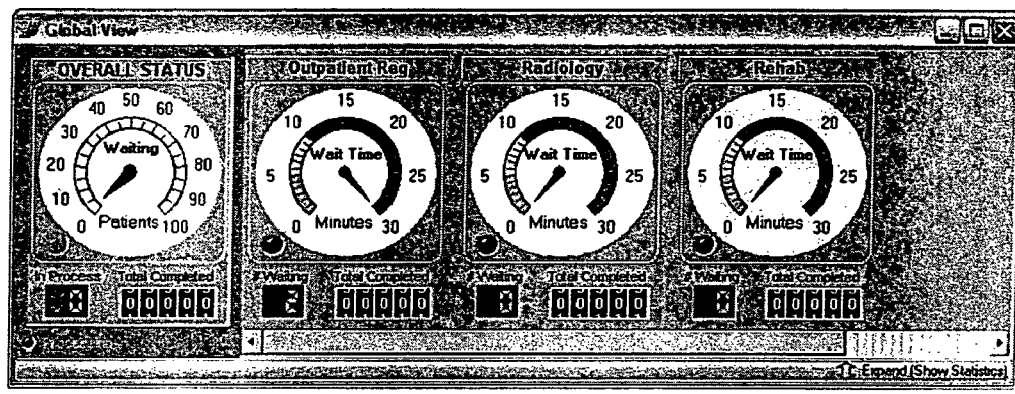
Figure 30:
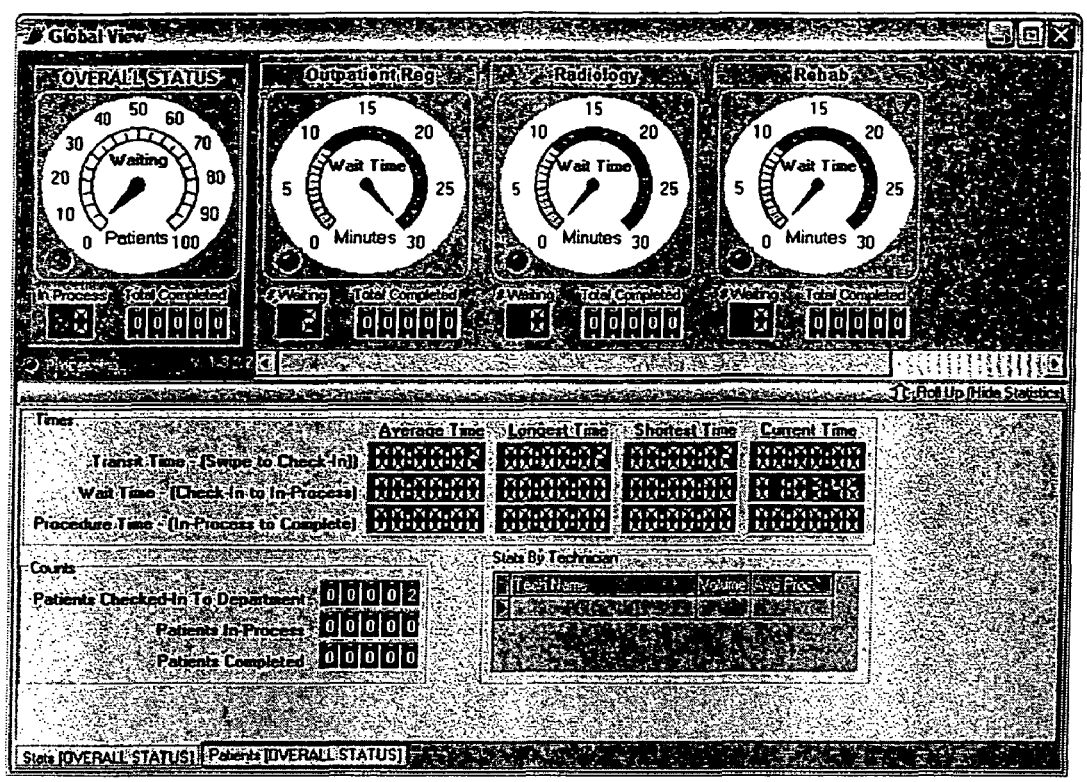

Each section is also preferably a mouse clickable button. Selecting any of these sections highlights that section identifying it for further inquiry activity, which is evidenced by the green light illuminating as shown in FIG. 29B. Positioning the cursor over the 'Expand (Show Statistics)' area located near the lower right side of the display and subsequently clicking on the bar results in the display expanding and revealing statistics for that particular area associated with the illuminated green light as shown in FIG. 30. Two tabs are displayed for the illuminated sections that are expanded: Stats and Patients. The Stats tab provides a variety of computed statistical data for the selected area. This tab is grouped into three categories: Times, Counts, Stats by Technician. The "Times" Area includes these times as defined: a) Transit Time—(Swipe to Check-In), b) Wait Time—(Check-In to In-Process), and c) Procedure Time—(In-Process to Complete). Computations are performed to display the average, longest, shortest and current times for each category noted above. The "Counts" Area includes a display of the current number or count of Patients Checked-in to that area (Overall, Department or Ancillary depending on initial selection), the number of In-process patients, and the number of Completed patients. The "Stats by Technician" Area includes a scrollable window that contains the name of the registrar or technician for the area displayed along with the number of patients processed and the average process time for that individual registrar or technician. These statistics are updated on a regular basis using real-time data at the interval specified for that workstation.

Figure 31:
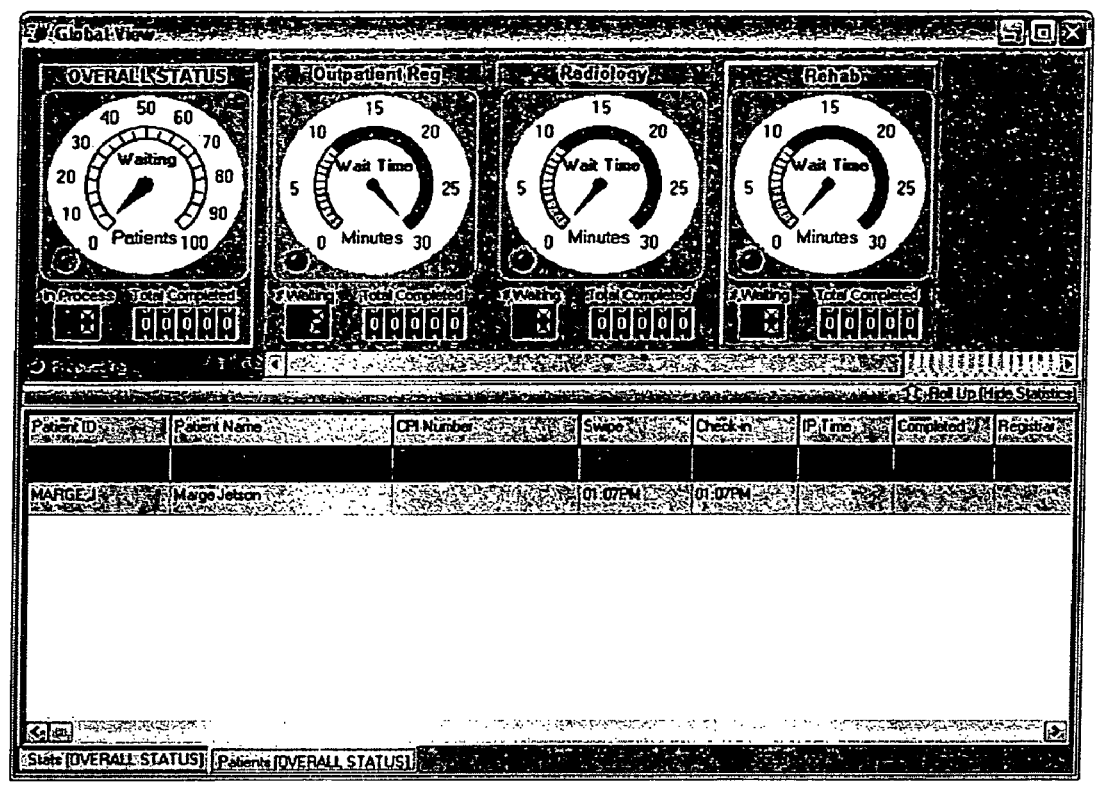

The Patients tab (FIG. 31) displays the detailed patient data in an inquiry only format similar (if not identical) to that displayed by the QueueView™ application described above. Patients that have been waiting for a period of time that falls within the predefined criteria according to the user-defined business rules display in the color corresponding to that business rule.

Figure 32A:
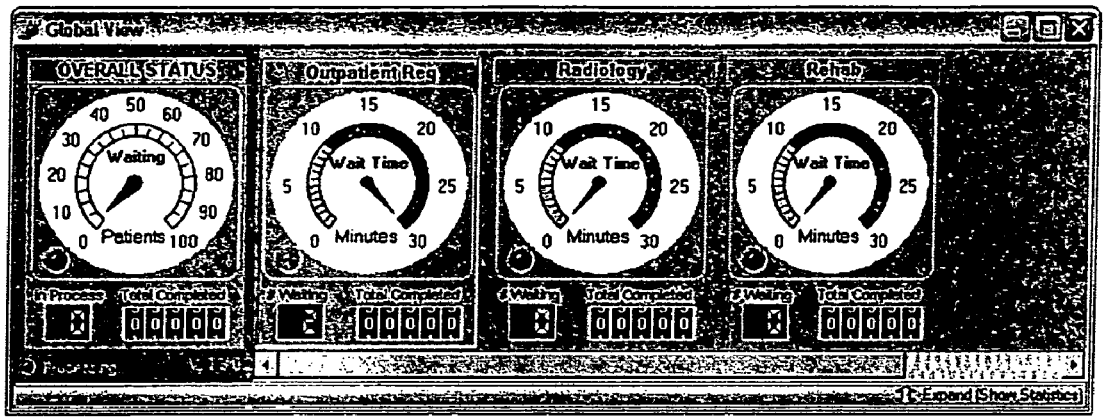
Figure 32B:
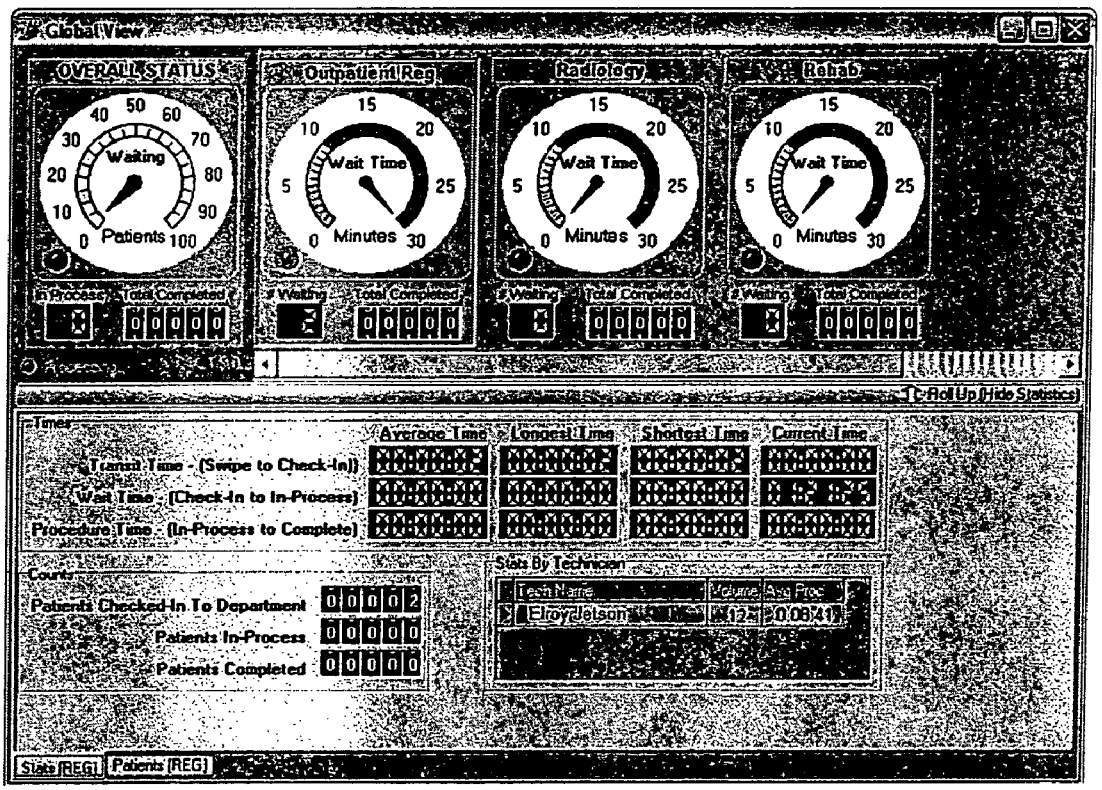
Figure 33A:
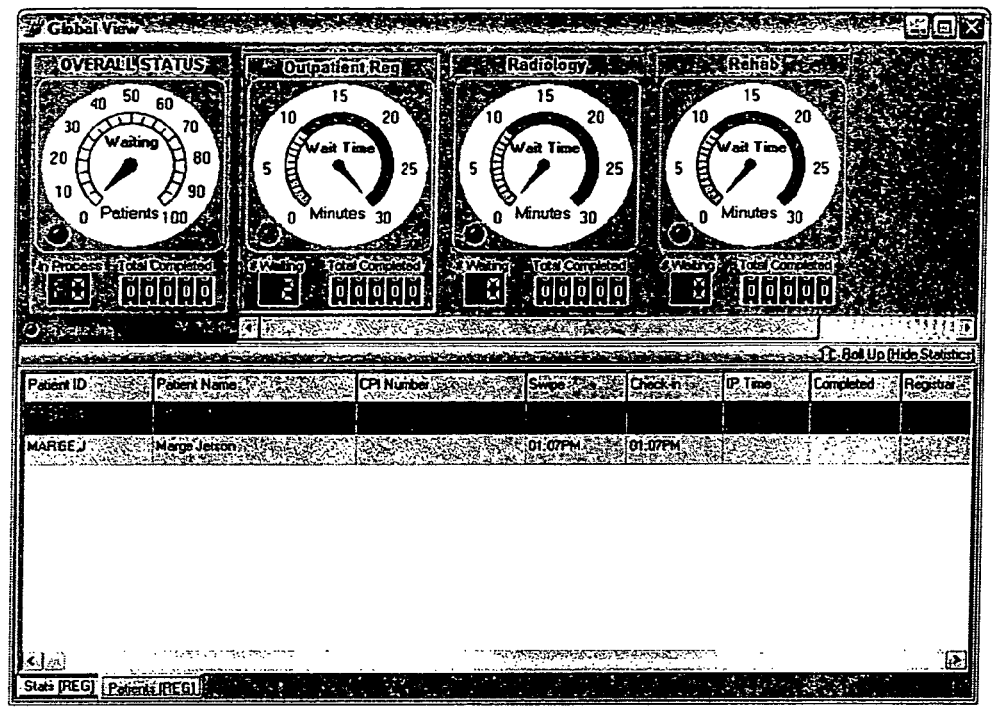
Figure 33B:
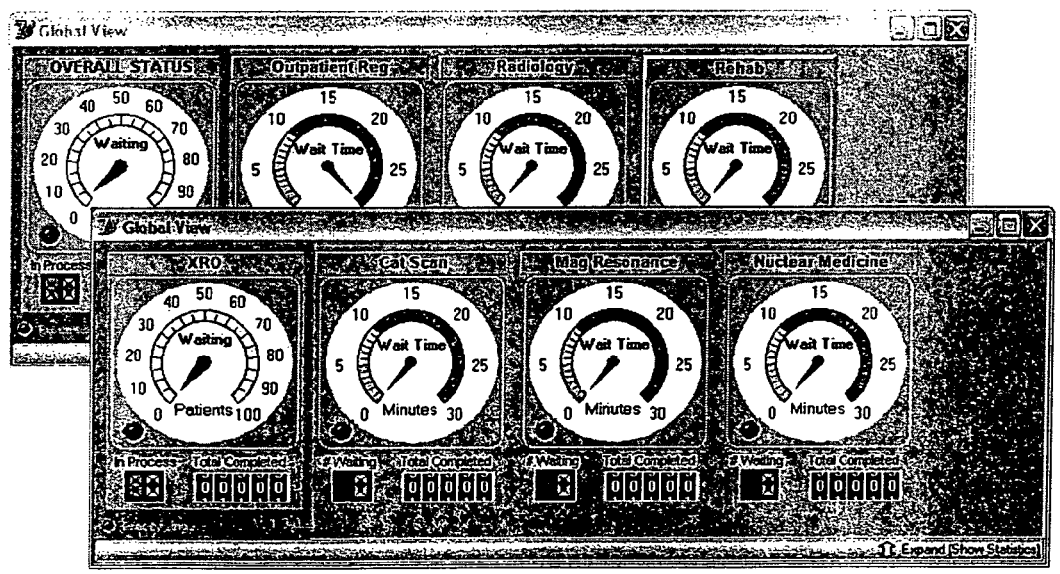

There are certain areas that can be selected that have a set of departments reporting up to them. Selecting one of these shows the resultant displays reflecting statistical data that is relevant to that particular area. In the screen shown in FIG. 32A, a Registration area or queue has been selected. In FIG. 32B, the 'Expand (Show Statistics)' with the 'Stats' tab has been selected. In FIG. 33A, the 'Expand (Show Statistics)' with the "Patients" tab has been selected for the same Registration area or queue. If the area selected is an Ancillary area that has been built with Modalities associated with the area or queue then a new window opens as a result leaving the original display on the screen shown in FIG. 33B.

Figure 34A:
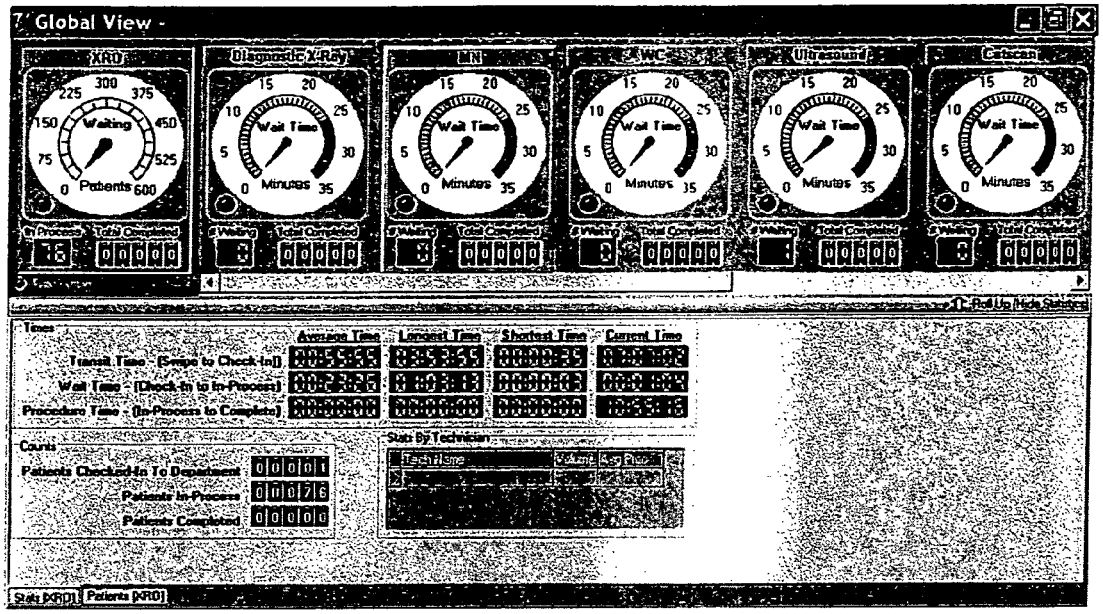
Figure 34B:
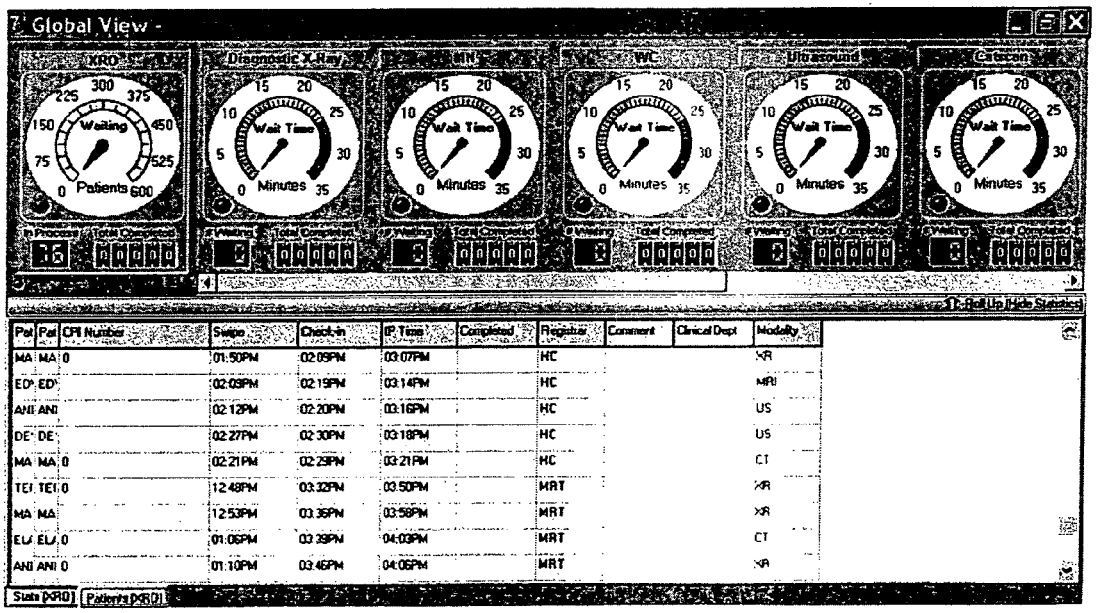

In the example above, 'Radiology' was highlighted and then selected with the resultant new window being opened that included all of the modalities associated with the Radiology queue being placed on the desktop directly beneath the original display. As is the case with the Registration area or queue displays, the modality displays also permit the selection of the statistical or patient detail tabs that contain data relevant to the area or in this case, modality selected. Displays of both statistical and patient tabs are shown in FIGS. 34A and 34B.

Figures 35A, 35B:
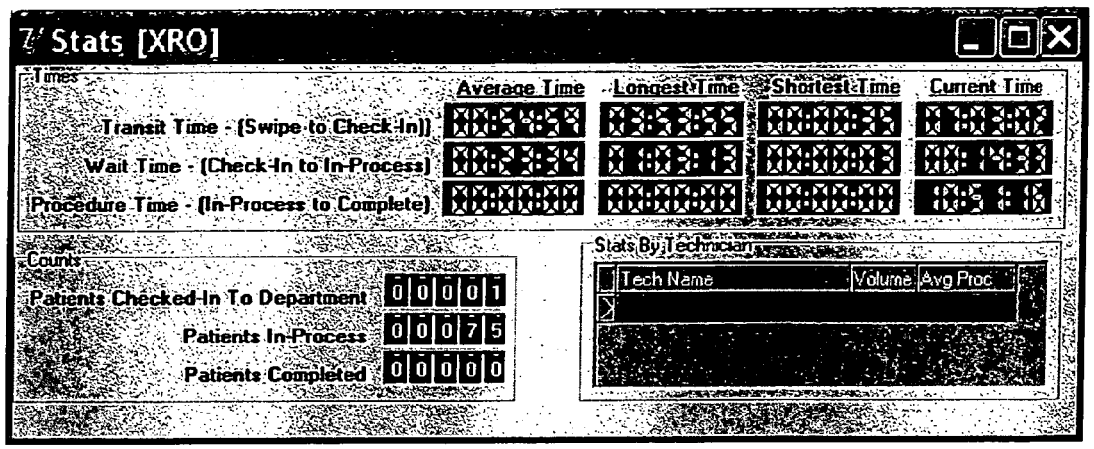

The system provides constant detail monitoring. By placing the cursor over the 'Stats' tab, clicking and holding the left mouse button and dragging, the entire window can be undocked and placed in a convenient location on the Windows desktop space. Similarly, this function can be performed for the 'Patients' tab as well as shown in FIGS. 35A and 35B.

Figure 36A:
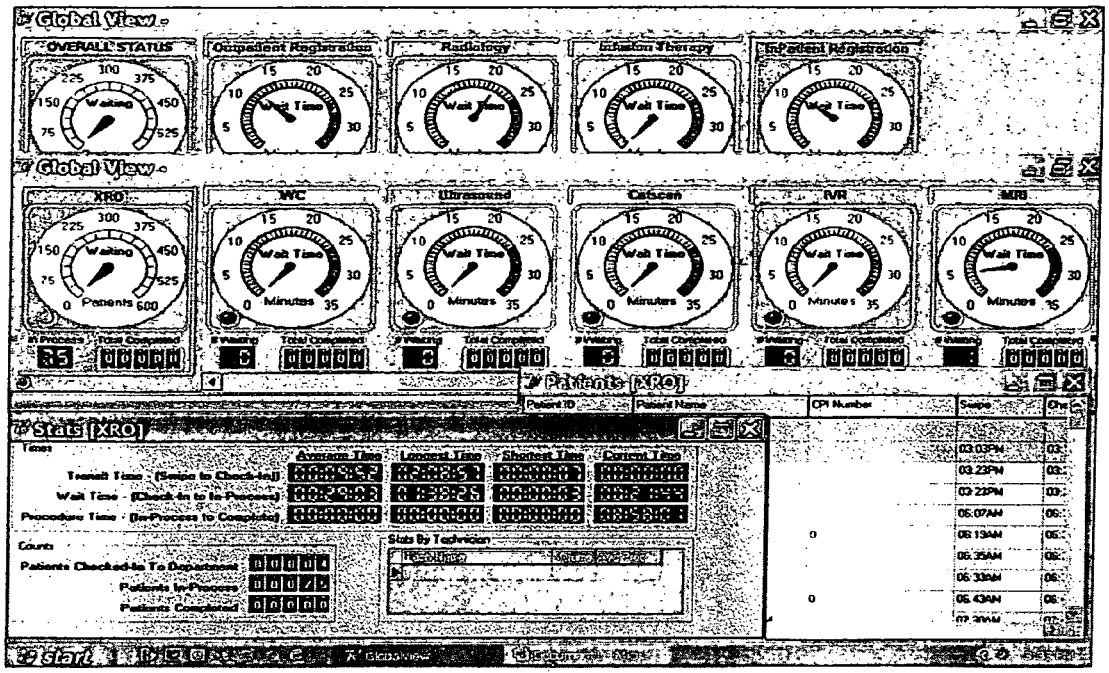
Figure 36B:
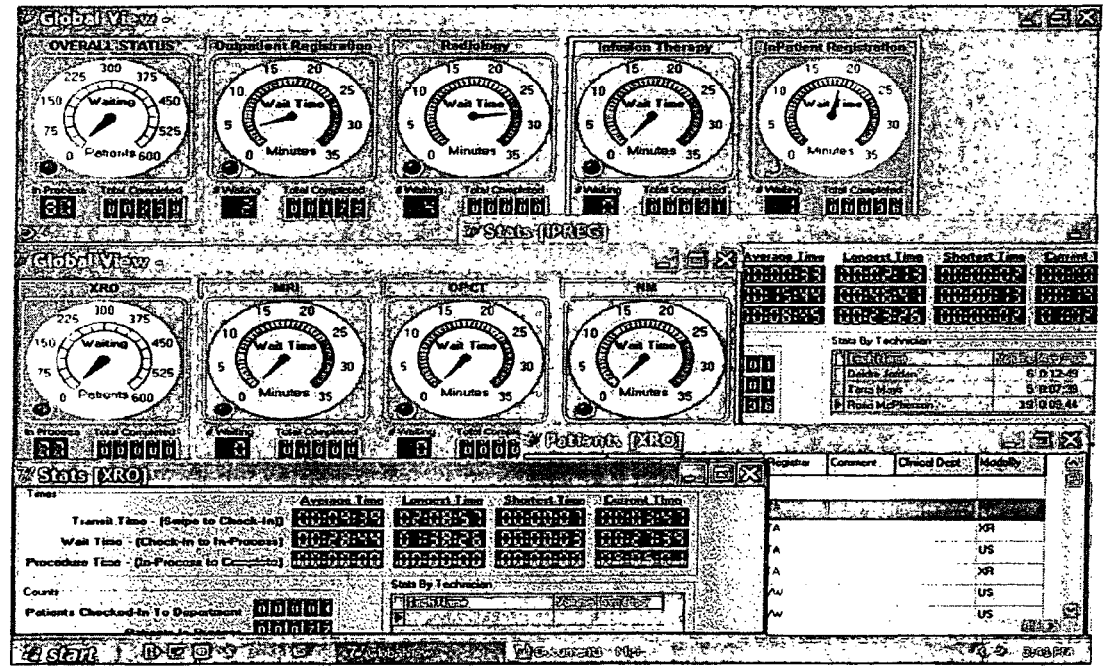

The ability to define the placement of these windows away from the primary window provides the User with the capability to open multiple windows and thus gain visibility into multiple patient registration and ancillary areas and monitor statistics related to these areas on a real time basis as shown in FIGS. 36A and 36B.

EXAMPLE 6

System Advertising Module

A System Advertising Module provides for advertising, which is facilitated by hardware and software components of the system of the invention. This advertising can take place on a large screen (located in waiting areas). Along with the status of the patient, some portion of the screen is utilized to provide the following examples of information: news, weather, registration requests and advertisements. This information is displayed in configurable, time-based increments on any of the system output devices. This advertising can also take place on a kiosk such that advertising messages are displayed in short bursts on the kiosk screen during the patient's usage of the kiosk. This advertising can also take place on printed material (e.g., any printed material which is provided by the system may contain advertising material). This advertising is beneficial to the advertiser in several ways.

The Advertising talks directly to a specific audience. The system of the invention collects data regarding the profile of the institution's traffic. This profile information is a valuable tool in aiming advertising campaigns directly at a target audience. Specific patient traffic is perceived by the advertiser as: specific target viewer ship, ability to create direct product and brand awareness to this specific target audience, creation of product and brand influence and in some cases, the patient asking the clinician for a specific product. Also, advertising via the system of the invention provides the "Last Point of Communication" directly to a possible product user prior to that individual's meeting with a clinician. This advertising allows the product brand to "Own the Environment." This advertising specifically addresses all three of the advertiser's desires regarding exposure. These desires are for exposure: prior to diagnosis, after diagnosis, but prior to treatment, and regarding persistency of treatment. This is highly sought after in that it will turn a drug into the compliant mean of treating a medical condition.

This Advertising Module can provide direct financial value to the healthcare institution in several ways. The institution can develop a pricing model and invoice the advertiser for this service. This invoicing may occur via the profile and traffic that actually exposes to the components of this advertising. The advertiser pays for what they actually receive. The advertiser may decide to provide the system of the invention for an institution gratis. In return, the advertiser receives some amount of advertising on the system components.

Other Embodiments

This description has been by way of example of how the devices, processes and methods of the invention can be made and carried out. Various details may be modified in arriving at the other detailed embodiments, and many of these embodiments will come within the scope of the invention. Therefore, to apprise the public of the scope of the invention and the embodiments covered by the invention, the following claims are made.

What is claimed is:

1. A process for managing and tracking flow of patients throughout a healthcare enterprise comprising:
    providing computer network implemented software adapted to enter, process, retrieve, transfer, store and display data related to said enterprise and related to each of said patients who is in need of one or more health care services, said software performing the steps of:
    providing a unique patient identifier associated with each of said patients and creating a list of patient identifiers;
    checking-in each of said patients and creating from said list a patient queue comprising a list of patient identifiers corresponding to each checked-in patient;
    determining each health care service needed by each of said patients in need of one or more health care services;
    associating each health care service needed by each of said patients with one of a plurality of health care service departments of said healthcare enterprise;
    creating a health care service department queue for each department of said plurality of departments;
    determining efficiency of each health care service department in providing health care services by applying to each health care service department queue department priority selection rules for placing patients awaiting service at an assigned patient queue position, said selection priority based on data representative of and selected from the group consisting essentially of expected department waiting times, patient placement on said patient queue, notifications, VIP status, special handling criteria, scheduled versus unscheduled status, card privileges, management notifications, administration notifications, status queue changes, wait time criteria and whether a patient has not completed visits to all departments;
    linking said patient queue to each department queue;
    matching said patient queue for each patient who remains in need of a health care service to each corresponding department queue to provide matched patient and department queues;
    applying said priority rules to each of said matched patient and department queues to determine an expected priority position for each said patient on each said department queue;
    based on said expected priority position for each said patient, selecting one of said departments as a next receiving department for each said patient; and,
    routing each said patient to said next receiving department.

* * * * *